(12) United States Patent
Berme et al.

(10) Patent No.: US 9,622,686 B1
(45) Date of Patent: Apr. 18, 2017

(54) GAIT PERTURBATION SYSTEM AND A METHOD FOR TESTING AND/OR TRAINING A SUBJECT USING THE SAME

(71) Applicant: Bertec Corporation, Columbus, OH (US)

(72) Inventors: Necip Berme, Worthington, OH (US); Jaswandi Tushar Pitale, Hilliard, OH (US); Haluk Ay, Glendale, CA (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 15/095,040

(22) Filed: Apr. 9, 2016

(51) Int. Cl.
*A61B 5/11* (2006.01)
*A63B 26/00* (2006.01)

(52) U.S. Cl.
CPC ............ *A61B 5/112* (2013.01); *A63B 26/003* (2013.01)

(58) Field of Classification Search
CPC ............................. A61B 5/112; A63B 26/003
USPC ....................................................... 482/1, 7
See application file for complete search history.

(56) References Cited

U.S. PATENT DOCUMENTS

| | | | |
|---|---|---|---|
| 6,038,488 A | 3/2000 | Barnes et al. |
| 6,113,237 A | 9/2000 | Ober et al. |
| 6,152,564 A | 11/2000 | Ober et al. |
| 6,295,878 B1 | 10/2001 | Berme |
| 6,354,155 B1 | 3/2002 | Berme |
| 6,389,883 B1 | 5/2002 | Berme et al. |
| 6,936,016 B2 | 8/2005 | Berme et al. |
| 8,181,541 B2 | 5/2012 | Berme |
| 8,315,822 B2 | 11/2012 | Berme et al. |
| 8,315,823 B2 | 11/2012 | Berme et al. |
| D689,388 S | 9/2013 | Berme |
| D689,389 S | 9/2013 | Berme |
| 8,543,540 B1 | 9/2013 | Wilson et al. |
| 8,544,347 B1 | 10/2013 | Berme |
| 8,622,747 B2 | 1/2014 | Chu et al. |
| 8,643,669 B1 | 2/2014 | Wilson et al. |
| 8,700,569 B1 | 4/2014 | Wilson et al. |
| 8,704,855 B1 | 4/2014 | Berme et al. |
| 8,764,532 B1 | 7/2014 | Berme |
| 8,847,989 B1 | 9/2014 | Berme et al. |
| D715,669 S | 10/2014 | Berme |
| 8,902,249 B1 | 12/2014 | Wilson et al. |
| 8,915,149 B1 | 12/2014 | Berme |

(Continued)

*Primary Examiner* — Sandhara Ganesan
(74) *Attorney, Agent, or Firm* — The Law Office of Patrick F. O'Reilly III, LLC

(57) ABSTRACT

A gait perturbation system and a method for testing and/or training using the gait perturbation system is disclosed herein. The gait perturbation system includes a gait perturbation device and a data processing device. The gait perturbation device includes one or more displaceable components configured to be displaced at a plurality of different speeds, and having one or more respective surfaces for receiving one or more respective limbs of a person; and one or more speed adjustment mechanisms coupled to the one or more displaceable components to adjust the speed set point at which the one or more displaceable components are displaced. The data processing device is configured to generate a signal for introducing a perturbation to the one or more displaceable components, and to control the speed set point of the one or more displaceable components such that the one or more displaceable components perturb a gait of the person.

20 Claims, 12 Drawing Sheets

(56) References Cited

U.S. PATENT DOCUMENTS

| | | |
|---|---|---|
| 9,032,817 B2 | 5/2015 | Berme et al. |
| 9,043,278 B1 | 5/2015 | Wilson et al. |
| 9,066,667 B1 | 6/2015 | Berme et al. |
| 9,081,436 B1 | 7/2015 | Berme et al. |
| 9,168,420 B1 | 10/2015 | Berme et al. |
| 9,173,596 B1 | 11/2015 | Berme et al. |
| 9,200,897 B1 | 12/2015 | Wilson et al. |
| 9,277,857 B1 | 3/2016 | Berme et al. |
| D755,067 S | 5/2016 | Berme et al. |
| 2003/0110148 A1* | 6/2003 | Ulyanov ............ B60G 17/0182 706/2 |
| 2003/0216656 A1 | 11/2003 | Berme et al. |
| 2008/0228110 A1 | 9/2008 | Berme |
| 2011/0277562 A1 | 11/2011 | Berme |
| 2011/0312473 A1* | 12/2011 | Chu ................... A63B 22/0292 482/54 |
| 2012/0266648 A1 | 10/2012 | Berme et al. |
| 2012/0271565 A1 | 10/2012 | Berme et al. |
| 2013/0132031 A1* | 5/2013 | Gilg ........................ G06F 17/13 702/181 |
| 2015/0096387 A1 | 4/2015 | Berme et al. |

\* cited by examiner

GAIT PERTURBATION SYSTEM AND A METHOD FOR TESTING AND/OR TRAINING A SUBJECT USING THE SAME

CROSS-REFERENCE TO RELATED APPLICATIONS

Not Applicable

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a gait perturbation system. More particularly, the invention relates to a gait perturbation system that is capable of perturbing a gait of a person.

2. Background and Description of Related Art

In order to study human motion, subjects are often tested in gait labs which are provided with special equipment disposed therein for measuring body movements, body mechanics, and/or the activity of the muscles (e.g., gait labs with force plates, etc.). The gait analysis performed in the gait lab is typically used to assess, plan, and/or treat subjects with medical conditions affecting their ability to walk. Also, the gait analysis is often used in sports biomechanics to improve athletic performance, and to help identify and/or treat injuries that deleteriously affect athletic performance.

However, the artificial nature of a typical environment for testing and/or training the gait of a subject (e.g., a typical gait lab) makes it difficult to simulate the real-life conditions that are encountered by the subject. Also, these artificial environments for gait testing and/or training are unable to effectively simulate the uncertain nature of the stimuli encountered by subjects in real-life scenarios. As such, these artificial gait testing and/or training environments are limited in their overall ability to effectively test and/or train subjects for the scenarios that are actually experienced by subjects in the their everyday lives.

Therefore, what is needed is a gait perturbation system that is capable of simulating real-life conditions by subjecting the person being tested to dynamic instability. Moreover, a gait perturbation system is needed that is capable of generating random stimuli in order to emulate real-life conditions encountered by the person undergoing testing. Furthermore, what is needed is a gait perturbation system that is capable of more effectively training a person with a gait disorder by delivering random stimuli to the person so that he or she is able to more effectively react to unpredictable disturbances that are encountered in real-life scenarios.

BRIEF SUMMARY OF EMBODIMENTS OF THE INVENTION

Accordingly, the present invention is directed to a gait perturbation system and a method for testing and/or training a subject using the same that substantially obviates one or more problems resulting from the limitations and deficiencies of the related art.

In accordance with one or more embodiments of the present invention, there is provided a gait perturbation system comprising a gait perturbation device and a data processing device. The gait perturbation device is configured to receive a person thereon, and the gait perturbation device includes one or more displaceable components configured to be displaced at a plurality of different speeds, the one or more displaceable components having one or more respective surfaces for receiving one or more respective limbs of the person; and one or more speed adjustment mechanisms coupled to the one or more displaceable components, the one or more speed adjustment mechanisms configured to adjust the speed set point at which the one or more displaceable components are displaced. The data processing device is operatively coupled to the one or more speed adjustment mechanisms, and the data processing device is configured to generate a first base velocity signal for controlling the speed of the one or more displaceable components and a second velocity signal for introducing a perturbation to the one or more displaceable components, the data processing device is further configured to combine the first base velocity signal with the second velocity signal to form a composite velocity signal, and to control the speed set point of the one or more displaceable components using the composite velocity signal such that the one or more displaceable components perturb a gait of the person.

In a further embodiment of the present invention, the gait perturbation device comprises a treadmill, and the one or more displaceable components comprise one or more belts of the treadmill; and the one or more speed adjustment mechanisms are configured to adjust the speed set point at which the one or more belts of the treadmill are rotated.

In yet a further embodiment, the treadmill comprises an instrumented treadmill, the instrumented treadmill including at least one force transducer, the at least one force transducer configured to sense one or more measured quantities and output one or more signals that are representative of one or more loads being applied to the one or more respective surfaces of the one or more belts of the treadmill by the person.

In still a further embodiment, the one or more speed adjustment mechanisms comprise one or more servo controllers configured to adjust the speed set point at which the one or more belts of the treadmill are rotated.

In yet a further embodiment, the second velocity signal generated by the data processing device comprises a stochastic signal.

In still a further embodiment, the stochastic signal comprises one of: (i) a uniform stochastic signal and (ii) a normal stochastic signal.

In yet a further embodiment, the gait perturbation system further comprises at least one input device, the at least one input device configured to enable a user to manually input at least one of: (i) an amplitude of the second velocity signal, (ii) a frequency of the second velocity signal, and (iii) a signal type of the second velocity signal, the signal type of the second velocity signal being selected from the group consisting of a uniform signal and a random signal.

In still a further embodiment, the data processing device is configured to generate the second velocity signal based upon at least one of: (i) the amplitude of the second velocity signal input by the user, (ii) the frequency of the second velocity signal input by the user, and (iii) the signal type of the second velocity signal input by the user.

In yet a further embodiment, the data processing device is configured to generate the second velocity signal based upon the amplitude of the second velocity signal input by the user, and at least one of: (i) the frequency of the second velocity signal input by the user, and (ii) the signal type of the second velocity signal input by the user.

In still a further embodiment, the second velocity signal comprises a uniform stochastic signal, the data processing device configured to compute the uniform stochastic signal as a function of a randomly generated uniform signal and the amplitude input by the user.

In yet a further embodiment, the second velocity signal comprises a normal stochastic signal, the data processing device configured to compute the normal stochastic signal as a function of a normalized randomly generated uniform signal and the amplitude input by the user.

In still a further embodiment, the gait perturbation system further comprises secondary means for displacing the one or more displaceable components of the gait perturbation device in a direction different from a primary direction of displacement of the one or more displaceable components, the secondary means for displacing the one or more displaceable components of the gait perturbation device being operatively coupled to the data processing device; and the data processing device being configured to generate a translation perturbation signal and to output the translation perturbation signal to the secondary means for displacing the one or more displaceable components of the gait perturbation device so that the one or more displaceable components of the gait perturbation device are displaced in a direction different from a primary direction of displacement of the one or more displaceable components.

In accordance with one or more other embodiments of the present invention, there is provided a gait perturbation system comprising a gait perturbation device and a data processing device. The gait perturbation device is configured to receive a person thereon, and the gait perturbation device includes one or more displaceable components configured to be displaced at a plurality of different speeds, the one or more displaceable components having one or more respective surfaces for receiving one or more respective limbs of the person; and one or more speed adjustment mechanisms coupled to the one or more displaceable components, the one or more speed adjustment mechanisms configured to adjust the speed set point at which the one or more displaceable components are displaced. The data processing device is operatively coupled to the one or more speed adjustment mechanisms, and the data processing device is configured to generate a stochastic signal for introducing a perturbation to the one or more displaceable components, the data processing device is further configured to control the speed set point of the one or more displaceable components using the stochastic signal such that the one or more displaceable components perturb a gait of the person.

In a further embodiment of the present invention, the gait perturbation device comprises a treadmill, and the one or more displaceable components comprise one or more belts of the treadmill; and the one or more speed adjustment mechanisms are configured to adjust the speed set point at which the one or more belts of the treadmill are rotated.

In yet a further embodiment, the treadmill comprises an instrumented treadmill, the instrumented treadmill including at least one force transducer, the at least one force transducer configured to sense one or more measured quantities and output one or more signals that are representative of one or more loads being applied to the one or more respective surfaces of the one or more belts of the treadmill by the person.

In still a further embodiment, the one or more speed adjustment mechanisms comprise one or more servo controllers configured to adjust the speed set point at which the one or more belts of the treadmill are rotated.

In yet a further embodiment, the stochastic signal generated by the data processing device comprises a uniform stochastic signal, the data processing device configured to compute the uniform stochastic signal as a function of a randomly generated uniform signal and an amplitude value input by a user using an input device operatively coupled to the data processing device.

In still a further embodiment, the stochastic signal generated by the data processing device comprises a normal stochastic signal, the data processing device configured to compute the normal stochastic signal as a function of a normalized randomly generated uniform signal and an amplitude value input by a user using an input device operatively coupled to the data processing device.

In accordance with yet one or more other embodiments of the present invention, there is provided a method for testing and/or training a person using a gait perturbation system. The method comprising the steps of: (i) providing a gait perturbation device configured to receive a person thereon, the gait perturbation device including one or more displaceable components configured to be displaced at a plurality of different speeds, the one or more displaceable components having one or more respective surfaces for receiving one or more respective limbs of the person; and one or more speed adjustment mechanisms coupled to the one or more displaceable components, the one or more speed adjustment mechanisms configured to adjust the speed set point at which the one or more displaceable components are displaced; (ii) providing a data processing device operatively coupled to the one or more speed adjustment mechanisms, the data processing device configured to generate a stochastic signal for introducing a perturbation to the one or more displaceable components, the data processing device further configured to control the speed set point of the one or more displaceable components using the stochastic signal such that the one or more displaceable components perturb a gait of the person; (iii) positioning the person on one or more respective surfaces of the one or more displaceable components of the gait perturbation device; (iv) generating, by using the data processing device, a stochastic signal for introducing a perturbation to the one or more displaceable components of the gait perturbation device; (v) controlling, by using the data processing device, the speed set point of the one or more displaceable components of the gait perturbation device using the stochastic signal; and (vi) displacing, by using the one or more speed adjustment mechanisms, the one or more displaceable components of the gait perturbation device based upon the speed set point determined using the stochastic signal such that the one or more displaceable components randomly perturb a gait of the person.

In a further embodiment of the present invention, the method further comprises the steps of: (vii) providing at least one input device operatively coupled to the data processing device, the at least one input device configured to enable a user to manually input at least one of: (a) an amplitude of the stochastic signal, (b) a frequency of the stochastic signal, and (c) a signal type of the stochastic signal, the signal type of the stochastic signal being selected from the group consisting of a uniform signal and a random signal; (viii) receiving, at the data processing device, the at least one of: (a) the amplitude of the stochastic signal, (b) the frequency of the stochastic signal, and (c) the signal type of the stochastic signal from the at least one input device; and (ix) generating, by using the data processing device, the stochastic signal based upon at least one of: (a) the amplitude of the stochastic signal, (b) the frequency of the stochastic signal, and (c) the signal type of the stochastic signal.

In yet a further embodiment, the stochastic signal generated by the data processing device comprises a uniform stochastic signal or a normal stochastic signal, wherein the data processing device is configured to generate the stochastic signal based upon the amplitude of the stochastic signal input by the user, and at least one of: (a) the frequency of the stochastic signal input by the user, and (b) the signal type of the stochastic signal input by the user; and wherein the method further comprises the step of: (vii) computing the uniform stochastic signal or the normal stochastic signal as a function of a randomly generated uniform signal and the amplitude input by the user.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
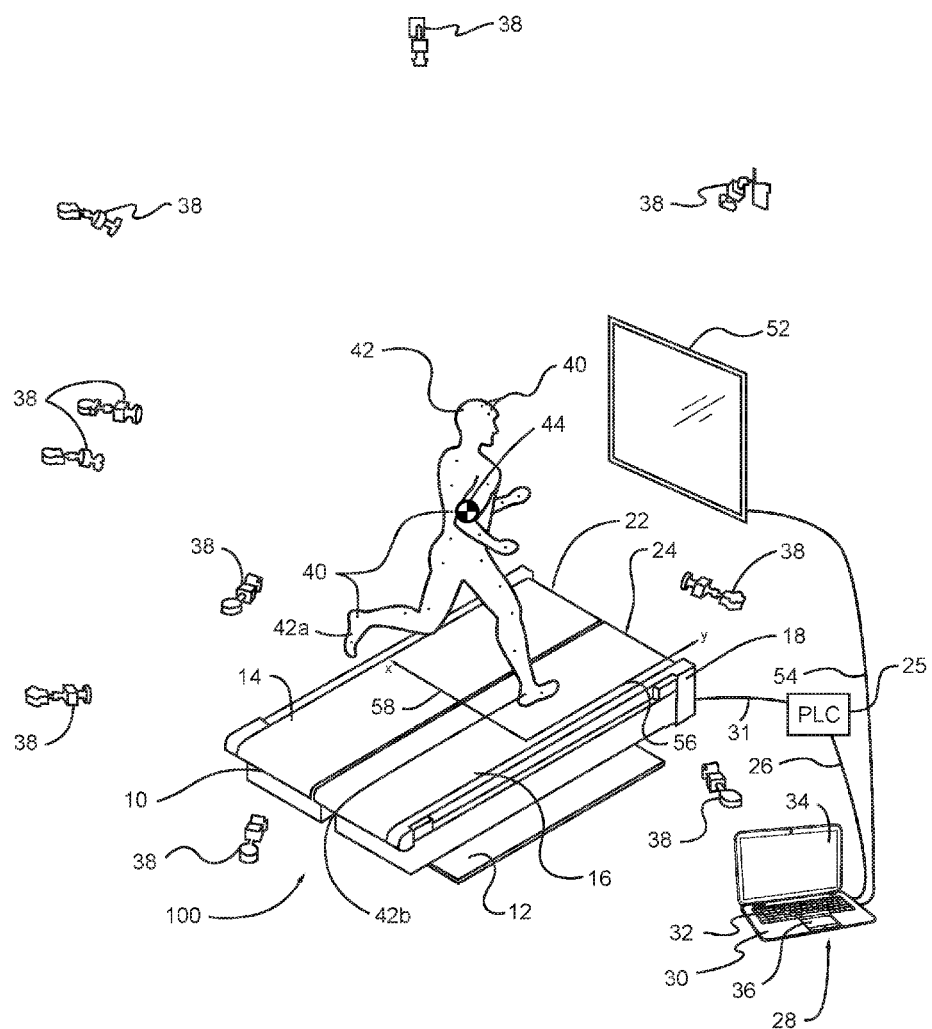
FIG. 1 is a perspective view of a gait perturbation system with a gait perturbation device in the form of an instrumented treadmill, according to an embodiment of the invention.

An illustrative embodiment of a gait perturbation system is seen generally at 100 in FIG. 1. In the illustrative embodiment of FIG. 1, the gait perturbation system 100 generally comprises a gait perturbation device 10 in the form of an instrumented treadmill that is operatively coupled to a data acquisition/data processing device 28 (i.e., a data acquisition and processing device or computing device that is capable of collecting, storing, and processing data), which in turn, is operatively coupled to a subject visual display device 52 for displaying images or scenes to the subject 42 disposed on the treadmill 10. The instrumented treadmill 10 is configured to receive a subject 42 thereon. As best illustrated in FIG. 1, the instrumented treadmill 10 is attached to the top of a base plate 12, which in turn, may be secured to a support surface (e.g., a building floor). The instrumented treadmill 10 has a plurality of top surfaces (i.e., left and right rotating belts 14, 16) that are each configured to receive a portion of a body of a subject 42 (e.g., the left belt 14 of the instrumented treadmill 10 is configured to receive a left leg of a subject 42, whereas the right belt 16 of the instrumented treadmill 10 is configured to receive a right leg of the subject 42).

In one or more embodiments, a subject walks or runs in an upright position atop the treadmill 10 with the feet 42a, 42b of the subject 42 contacting the respective top surfaces 22, 24 of the treadmill belts 14, 16. The belts 14, 16 of the treadmill 10 are rotated by independent electric actuator assemblies with one or more speed adjustment mechanisms (e.g., actuator control drive 27 in FIG. 6). In the illustrated embodiment, each electric actuator assembly comprises an electric motor operatively coupled to the actuator control drive 27. Under the control of the actuator control drive 27, each electric actuator assembly is capable of rotating its respective treadmill belt 14, 16 at a plurality of different speeds. The actuator control drive 27 (i.e., speed adjustment mechanism) adjusts the speed(s) at which each of the treadmill belts 14, 16 are rotated. The actuator control drive 27 (i.e., speed adjustment mechanism) of the instrumented treadmill 10 is operatively coupled to a programmable logic controller (PLC) 25 (see FIG. 6). The programmable logic controller 25 of the instrumented treadmill 10 is operatively connected to the data acquisition/data processing device 28 by an electrical cable 26, while the programmable logic controller 25 is operatively connected to the control portion 18 of the instrumented treadmill 10 (e.g., containing the actuator control drive 27) via an electrical cable 31 (see FIG. 1). While they are not readily visible in the perspective view of FIG. 1 due to their location, the instrumented treadmill 10 includes a plurality of force transducers (e.g., four (4) pylon-type force transducers 20—see e.g., FIGS. 2-4) disposed below each rotating belt 14, 16 of the treadmill 10 so that the loads being applied to the top surfaces 22, 24 of the belts 14, 16 can be measured. Advantageously, the separated belts 14, 16 of the instrumented treadmill 10 enable the forces and/or moments applied by the left and right legs of the subject 42 to be independently determined. As will be described in more detail hereinafter, the pylon-type force transducers 20 of the instrumented treadmill 10 are also operatively coupled to the treadmill programmable logic controller 25. In turn, the treadmill programmable logic controller 25 is operatively coupled to the data acquisition/data processing device 28 so that the force and moment output data of the pylon-type force transducers 20 is capable of being analyzed and processed by the data acquisition/data processing device 28.

Figure 2:
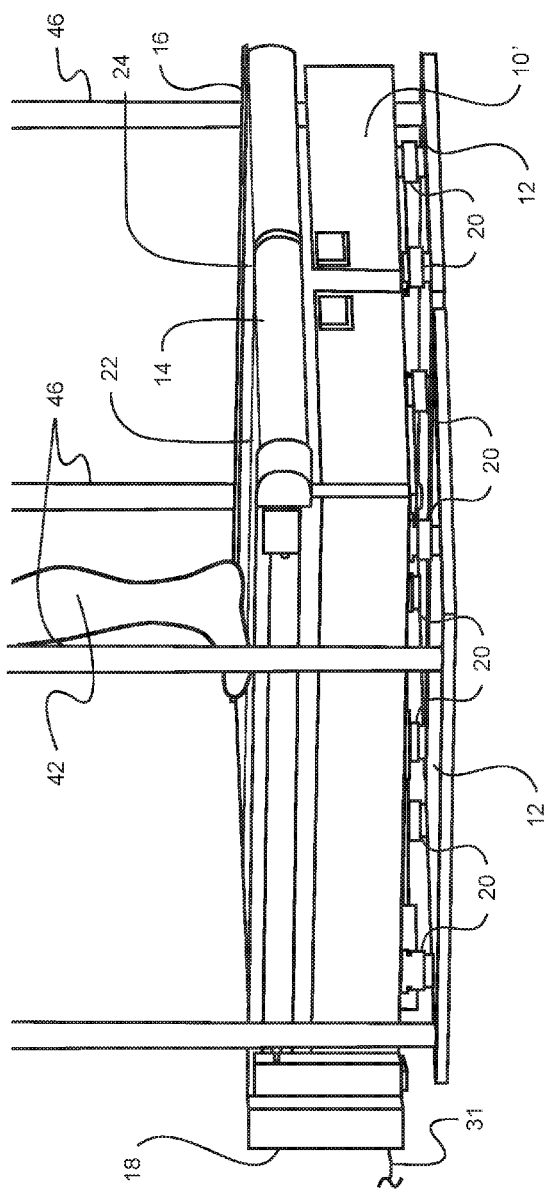
FIG. 2 is an end-side perspective view illustrating the pylon-type force transducers of the instrumented treadmill of FIG. 1, wherein, in this figure, handrails have been added to the instrumented treadmill of FIG. 1.
Figure 3:
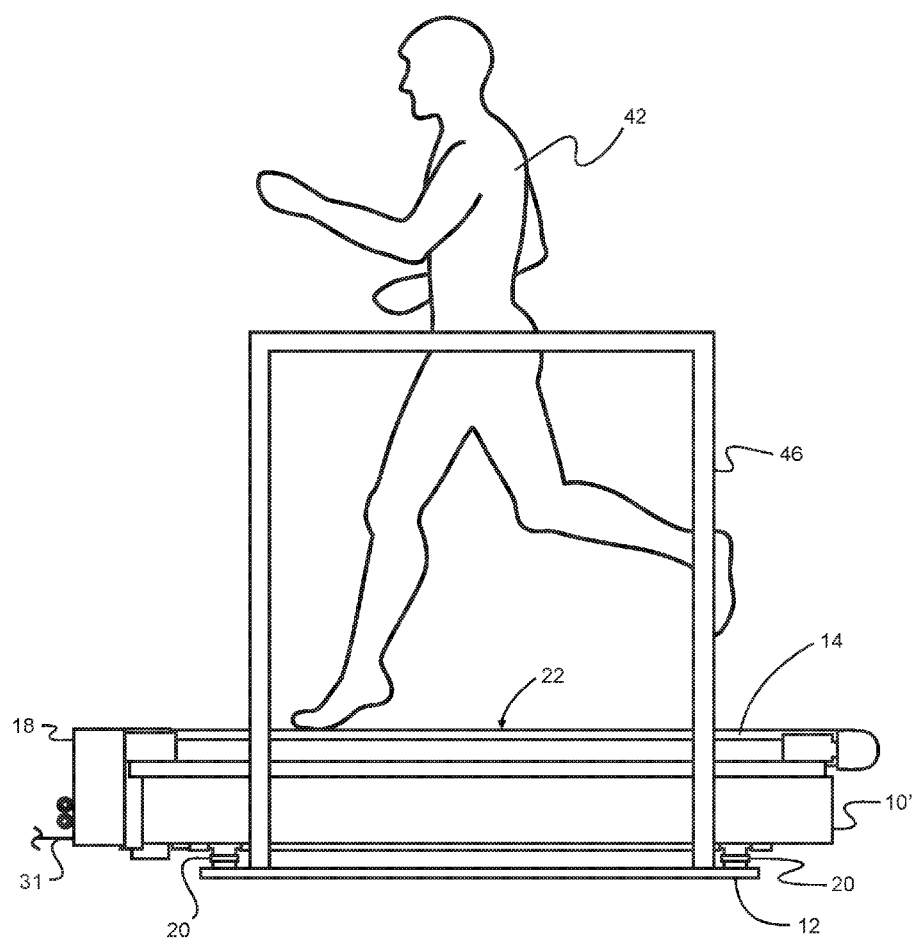
FIG. 3 is a side view illustrating the instrumented treadmill of FIG. 2.
Figure 4:
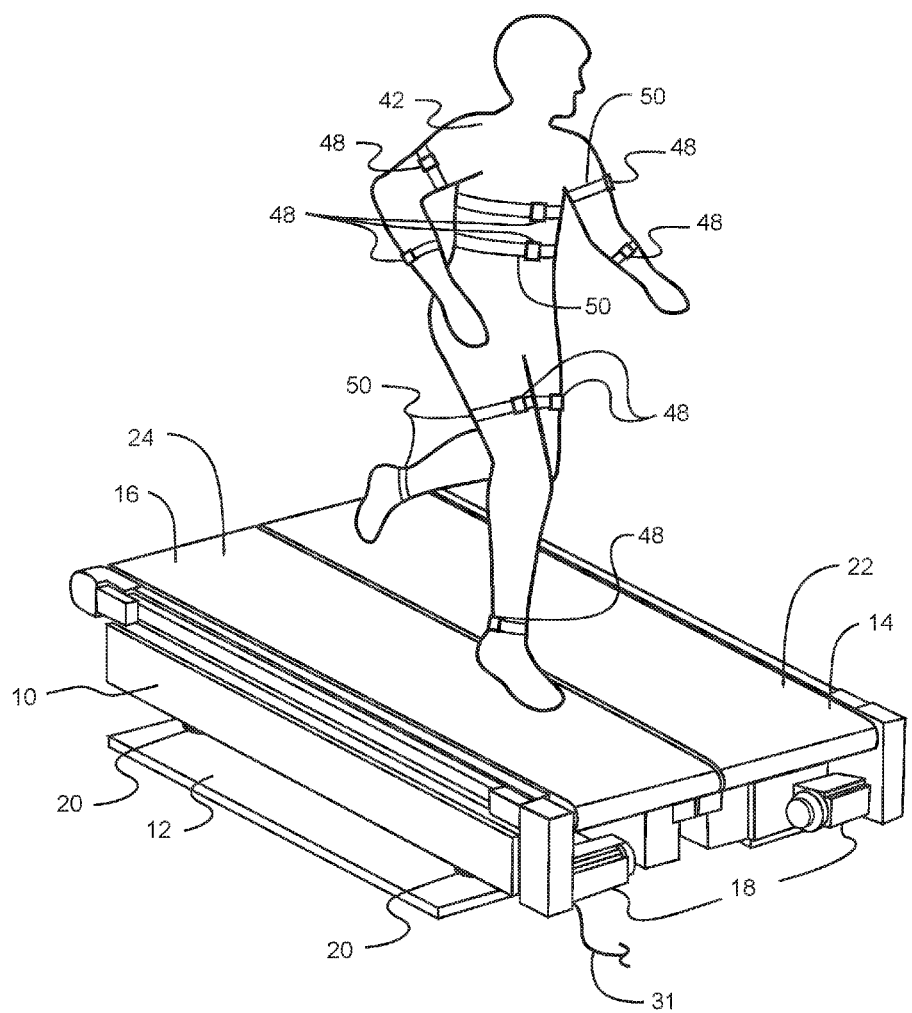
FIG. 4 is another perspective view of a subject disposed on the instrumented treadmill of FIG. 1, wherein the subject is outfitted with a plurality of inertial measurement units (IMUs) thereon.

As mentioned above, each of the treadmill belts 14, 16 is supported atop four (4) pylon-type force transducers 20 (or pylon-type load cells) that are disposed underneath, and near each of the four corners (4) of the left rotating belt 14 of the treadmill 10 and each of the four corners (4) of the right rotating belt 16 (see e.g., FIGS. 2-4). Each of the eight (8) pylon-type force transducers 20 has a plurality of strain gages adhered to the outer periphery of a cylindrically-shaped force transducer sensing element for detecting the mechanical strain of the force transducer sensing element imparted thereon by the force(s) applied to the belt surfaces 22, 24 of the instrumented treadmill 10. In the illustrative embodiment, each of the four (4) sets of pylon-type force transducers 20 are mounted atop the base plate 12.

In an alternative embodiment, rather than using four (4) pylon-type force transducers 20 on each treadmill belt assembly 14, 16, force transducers in the form of transducer beams could be provided under each treadmill belt assembly 14, 16. In this alternative embodiment, the left treadmill belt assembly 14 could comprise two transducer beams that are disposed underneath, and on generally opposite sides of the treadmill belt assembly 14. Similarly, in this embodiment, the right treadmill belt assembly 16 could comprise two transducer beams that are disposed underneath, and on generally opposite sides of the right treadmill belt assembly 16. Similar to the pylon-type force transducers 20, the force transducer beams could have a plurality of strain gages attached to one or more surfaces thereof for sensing the mechanical strain imparted on the beam by the force(s) applied to the surfaces 22, 24 of the instrumented treadmill 10.

Rather, than using four (4) force transducer pylons under each treadmill belt assembly 14, 16, or two spaced-apart force transducer beams under each treadmill belt assembly 14, 16, it is to be understood that the instrumented treadmill 10 can also utilize the force transducer technology described in U.S. Pat. No. 8,544,347, the entire disclosure of which is incorporated herein by reference.

In the illustrated embodiment, the electrical cable 26 mentioned above is used for the transmission of data between the programmable logic controller 25 and the data acquisition/data processing device 28, while the electrical cable 31 is used for the transmission of data between the instrumented treadmill 10 and the programmable logic controller 25. A separate power cable is used to provide power to the instrumented treadmill 10 (e.g., a power cable connected directly to the electrical power system of the building in which the treadmill 10 is disposed). While a hardwired data connection is provided between the programmable logic controller 25 and the data acquisition/data processing device 28 in the illustrative embodiment, it is to be understood that the programmable logic controller 25 can be operatively coupled to the data acquisition/data processing device 28 using other signal transmission means, such as a wireless data transmission system.

Figure 5:
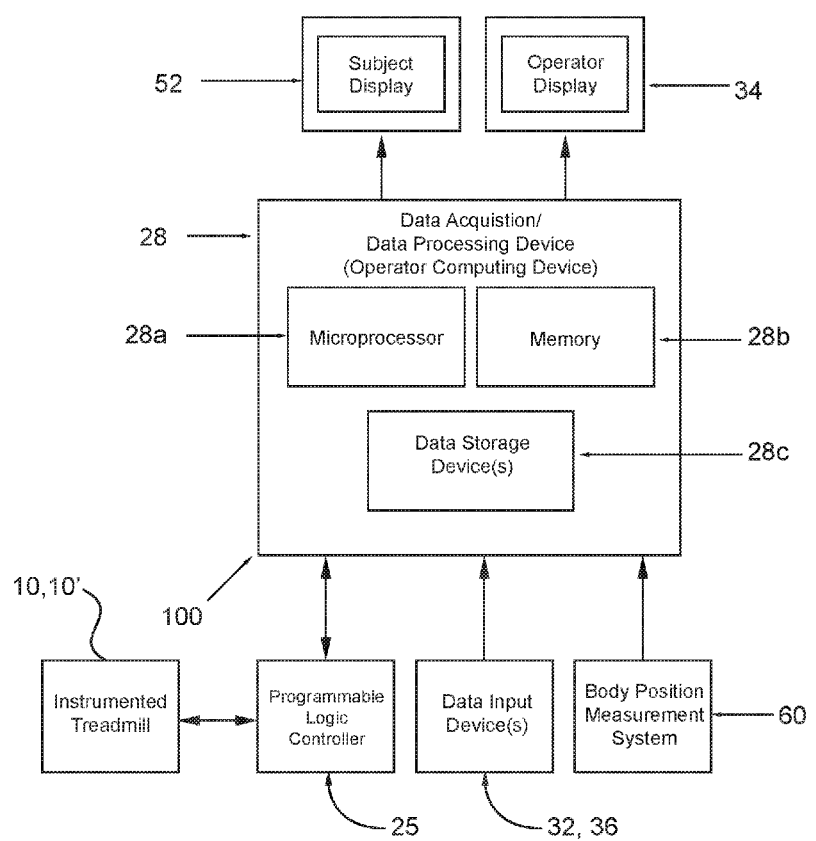
FIG. 5 is a block diagram of constituent components of the gait perturbation system with the instrumented treadmill of FIG. 1, according to an embodiment of the invention.

Now, turning to FIG. 5, it can be seen that the illustrated data acquisition/data processing device 28 (i.e., the operator computing device) of the gait perturbation system 100 includes a microprocessor 28a for processing data, memory 28b (e.g., random access memory or RAM) for storing data during the processing thereof, and data storage device(s) 28c, such as one or more hard drives, compact disk drives, floppy disk drives, flash drives, or any combination thereof. As shown in FIG. 1, the programmable logic controller (PLC) 25 of the instrumented treadmill 10, and the subject visual display device 52 are operatively coupled to the data acquisition/data processing device 28 such that data is capable of being transferred between these devices 25, 28, and 52. In FIG. 1, it can be seen that the programmable logic controller (PLC) 25 of the instrumented treadmill 10 is operatively coupled to the data acquisition/data processing device 28 by the electrical cable 26, while the subject visual display device 52 is operatively coupled to the data acquisition/data processing device 28 by the electrical cable 54. Also, as shown in FIG. 1, the data acquisition/data processing device 28 (e.g., in the form of a laptop digital computer) generally includes a base portion 30 with the microprocessor 28a disposed therein for collecting and processing the data that is received from the instrumented treadmill 10, and a plurality of devices 32-36 operatively coupled to the microprocessor 28a in the base portion 30. Preferably, the devices that are operatively coupled to the microprocessor 28a of the data acquisition/data processing device 28 comprise user input devices 32, 36 in the form of a keyboard 32 and a touchpad 36, as well as a graphical user interface in the form of a laptop LCD screen 34. While a laptop type computing system is depicted in FIG. 1, one of ordinary skill in the art will appreciate that another type of data acquisition/data processing device 28 can be substituted for the laptop computing system such as, but not limited to, a palmtop computing device (i.e., a PDA) or a desktop type computing system having a plurality of separate, operatively coupled components (e.g., a desktop type computing system including a main housing with a central processing unit (CPU) and data storage devices, a remote monitor, a remote keyboard, and a remote mouse). In addition, rather than providing a data acquisition/data processing device 28, it is to be understood that, in other embodiments, only a data acquisition device could be provided without departing from the spirit and the scope of the claimed invention.

Advantageously, the programmable logic controller 25 (see e.g., FIG. 6, which is a type of data processing device) provides real-time control of the treadmill actuators (i.e., motors) that control the rotation of the left and right treadmill belts 14, 16. The real-time control provided by the programmable logic controller 25 ensures that the software regulating the control of the left and right treadmill belts 14, 16 operates at the design clock rate, thereby providing fail-safe operation for subject safety. As such, user software applications that are being executed on the data acquisition/data processing device 28 do not interfere with the control of the left and right treadmill belts 14, 16. In one embodiment, the programmable logic controller 25 comprises both the treadmill control software and the input/output management software, which controls the functionality of the input/output (I/O) module of the programmable logic controller 25. In one embodiment, the programmable logic controller 25 utilizes EtherCAT protocol for enhanced speed capabilities and real-time control.

In one or more embodiments, the input/output (I/O) module of the programmable logic controller 25 allows various accessories to be added to the force measurement system 100. For example, an eye movement tracking system, such as that described by U.S. Pat. Nos. 6,113,237 and 6,152,564 could be operatively connected to the input/output (I/O) module of the programmable logic controller 25. As another example, a head movement tracking system, which is instrumented with one or more accelerometers, could be operatively connected to the input/output (I/O) module.

Figure 6:
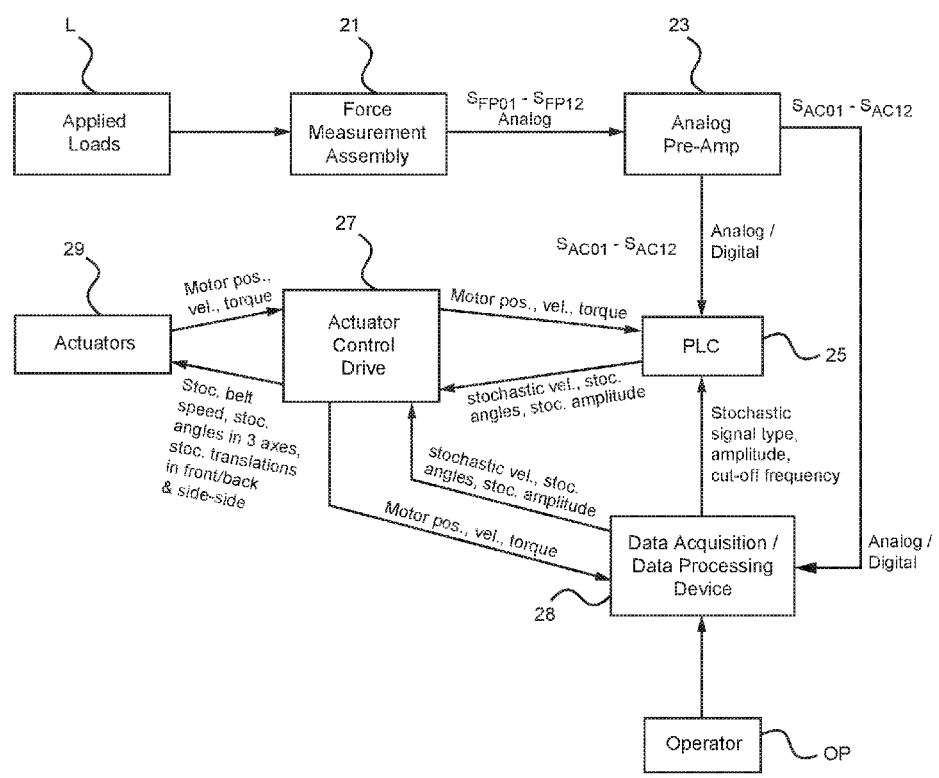
FIG. 6 is a block diagram illustrating the electronic actuator components of the instrumented treadmill of FIG. 1, and the data manipulation operations and motion control operations carried out by the gait perturbation system, according to an embodiment of the invention.

FIG. 6 graphically illustrates the acquisition and processing of the load data and the control of the actuators 29 carried out by the exemplary gait perturbation system 100. Initially, as shown in FIG. 6, a load L is applied to the treadmill force measurement assembly 21 by a subject disposed thereon. In the illustrative embodiment, the force measurement assembly 21 of the gait perturbation system 100 comprises the pylon-type force transducers 20 disposed underneath the treadmill belts 14, 16 described above. The load is transmitted from the treadmill belt assemblies 14, 16 to its respective set of pylon-type force transducers 20 (or force transducer beams). As described above, in the illustrated embodiment, each treadmill belt assembly 14, 16 comprises four (4) pylon-type force transducers 20 disposed thereunder. Preferably, these pylon-type force transducers 20 are disposed near respective corners of each treadmill belt assembly 14, 16. In a preferred embodiment, each of the pylon-type force transducers 20 includes a plurality of strain gages wired in one or more Wheatstone bridge configurations, wherein the electrical resistance of each strain gage is altered when the associated portion of the associated pylon-type force transducer undergoes deformation resulting from the load (i.e., forces and/or moments) acting on the treadmill belt assemblies 14, 16. For each plurality of strain gages disposed on the pylon-type force transducers 20, the change in the electrical resistance of the strain gages brings about a consequential change in the output voltage of the Wheatstone bridge (i.e., a quantity representative of the load being applied to the measurement surface). In one embodiment, the four (4) pylon-type force transducers 20 disposed under the treadmill belt assemblies 14, 16 output a total of twelve (12) output voltages (signals) in either analog or digital form. In some embodiments, if the output voltages (signals) are in analog form, the twelve (12) output voltages (signals) from the treadmill belt assemblies 14, 16 are then transmitted to a preamplifier board 23 for preconditioning. The preamplifier board 23 is used to increase the magnitudes of the transducer analog voltages. After which, in one or more embodiments, the analog output signals $S_{ACO1}$-$S_{AC12}$ are transmitted from the analog preamplifier 23 to the treadmill programmable logic controller (PLC) 25. In the treadmill programmable logic controller 25, the analog output signals $S_{ACO1}$-$S_{AC12}$ may be converted into forces, moments, centers of pressure (COP), subject center of gravity (COG), and/or sway angle for the subject. Then, the forces, moments, centers of pressure (COP), subject center of gravity (COG) 44 (see FIG. 1), and/or sway angle for the subject 42 computed by the programmable logic controller 25 are transmitted to the data acquisition/data processing device 28 (operator computing device 28) so that they can be utilized for analyzing the movement of the subject 42 and/or for reports displayed to an operator or clinician. Also, in yet another embodiment, the preamplifier board additionally could be used to convert the analog voltage signals into digital voltage signals (i.e., the preamplifier board could be provided with an analog-to-digital converter). In this embodiment, digital voltage signals would be transmitted to the treadmill programmable logic controller 25 rather than analog voltage signals.

In one or more embodiments, as shown in FIG. 6, when the programmable logic controller 25 receives the voltage signals $S_{ACO1}$-$S_{AC12}$, it initially transforms the signals into output forces and/or moments by multiplying the voltage signals $S_{ACO1}$-$S_{AC12}$ by a calibration matrix. After which, the force and moment components (i.e., $F_{Lx}$, $F_{Ly}$, $F_{Lz}$, $M_{Lx}$, $M_{Ly}$, $M_{Lz}$) exerted on the left belt surface 22 of the left treadmill belt assembly 14 by the left foot of the subject, the force and moment components (i.e., $F_{Rx}$, $F_{Ry}$, $F_{Rz}$, $M_{Rx}$, $M_{Ry}$, $M_{Rz}$) exerted on the right belt surface 24 of the right treadmill belt assembly 16 by the right foot of the subject, and the center of pressure ($x_{P_L}$, $y_{P_L}$; $x_{P_R}$, $y_{P_R}$) for each foot of the subject (i.e., the x and y coordinates of the point of application of the force applied to the measurement surface by each foot) are determined by the programmable logic controller 25, and then transmitted to the data acquisition/data processing device 28.

In one or more alternative embodiments, as also shown in FIG. 6, the voltage signals $S_{ACO1}$-$S_{AC12}$ may be transmitted to the data acquisition/data processing device 28, rather than to the programmable logic controller 25. In these one or more alternative embodiments, when the data acquisition/data processing device 28 receives the signals $S_{ACO1}$-$S_{AC12}$, it initially transforms the signals $S_{ACO1}$-$S_{AC12}$ into output forces and/or moments by multiplying the voltage signals $S_{ACO1}$-$S_{AC12}$ by the calibration matrix. After which, the force and moment components (i.e., $F_{Lx}$, $F_{Ly}$, $F_{Lz}$, $M_{Lx}$, $M_{Ly}$, $M_{Lz}$) exerted on the left belt surface 22 of the left treadmill belt assembly 14 by the left foot of the subject, the force and moment components (i.e., $F_{Rx}$, $F_{Ry}$, $F_{Rz}$, $M_{Rx}$, $M_{Ry}$, $M_{Rz}$) exerted on the right belt surface 24 of the right treadmill belt assembly 16 by the right foot of the subject, and the center of pressure ($x_{P_L}$, $y_{P_L}$; $x_{P_R}$, $y_{P_R}$) for each foot of the subject (i.e., the x and y coordinates of the point of application of the force applied to the measurement surface by each foot) are determined by the data acquisition/data processing device 28.

Also, in one or more embodiments, as shown in the perspective view of FIG. 1, the overall center of pressure ($x_P$, $y_P$) may also be determined for the subject 42 in accordance with the overall x-coordinate axis 58 and overall y-coordinate axis 56 disposed on the surface of the instrumented treadmill 10.

In the illustrated embodiment, the programmable logic controller 25 converts the computed center of pressure (COP) to a center of gravity (COG) for the subject using a Butterworth filter. For example, in one exemplary, non-limiting embodiment, a second-order Butterworth filter with a 0.75 Hz cutoff frequency is used. In addition, the programmable logic controller 25 also computes a sway angle for the subject using a corrected center of gravity (COG') value, wherein the center of gravity (COG) value is corrected to accommodate for the offset position of the subject relative to the origin of the coordinate axes (56, 58) of the treadmill force measurement assembly 21. For example, the programmable logic controller 25 computes the sway angle for the subject in the following manner:

$$\theta = \sin^{-1}\left(\frac{COG'}{0.55h}\right) - 2.3° \quad (1)$$

where:
θ: sway angle of the subject;
COG': corrected center of gravity of the subject; and
h: height of the center of gravity of the subject.

Now, referring again to the block diagram of FIG. 6, the manner in which the perturbations of the instrumented treadmill 10 are controlled will be explained. Initially, an operator OP inputs one or more motion commands (e.g., start/stop of treadmill belts 14, 16) and/or stochastic signal parameters (e.g., stochastic signal type, amplitude, and cutoff frequency) at the operator computing device 28 (data acquisition/data processing device 28) by utilizing one of the user input devices 32, 36. Once, the one or more motion commands and/or stochastic signal parameters are received at the operator computing device 28, the one or more motion commands and/or stochastic signal parameters are transmitted to the programmable logic controller 25. Then, after further processing by the programmable logic controller 25, the motion command signals (e.g., the one or more base velocity and stochastic signals including the stochastic velocity, stochastic angles, and stochastic amplitude) are transmitted to the actuator control drive 27. Alternatively, when the data acquisition/data processing device 28 generates the stochastic signal rather than the programmable logic controller 25, the motion command signals (e.g., the one or more base velocity and stochastic signals including the stochastic velocity, stochastic angles, and stochastic amplitude) are transmitted from the data acquisition/data processing device 28 directly to the actuator control drive 27, rather than to the programmable logic controller 25. Finally, the actuator control drive 27 transmits the direct-current (DC) motion command signals to the actuators 29 so that the treadmill belts 14, 16, and the subject 42 disposed thereon, can be displaced in the desired manner. The actuator control drive 27 controls the position, velocity, and torque of each actuator motor. Also, as shown in FIG. 6, the motion command signals sent from the actuator control drive 27 to the treadmill actuators 29 may include any one or all of the following: (i) the stochastic belt speed(s), (ii) stochastic angles in three (3) axes, and (iii) stochastic translations in front-to-back and side-to-side directions. In the illustrative embodiment, each of the treadmill belts 14, 16 may be provided with a dedicated rotational actuator 29 for the controlling the belt speeds thereof. In addition, the instrumented treadmill 10 may be provided with three (3) or more actuators 29 for rotating the instrumented treadmill 10 about the x, y, and z-coordinate axes, one or more translational actuators 29 for displacing the instrumented treadmill 10 in a front-to-back direction, and one or more translational actuators 29 for displacing the instrumented treadmill 10 in a side-to-side direction (i.e., secondary means for displacing the one or more displaceable components of the gait perturbation device in a side-to-side direction different from the primary front-to-back direction of the displacement of the belts 14, 16). Referring again to FIG. 6, in the alternative embodiment, it can be seen that the stochastic velocity, stochastic angles, and the stochastic amplitude may be transmitted directly from the operator computing device 28 to the actuator control drive 27 for controlling the actuators 29. The actuators 29 for rotating the instrumented treadmill 10 about the x, y, and z-coordinate axes, and for translating the treadmill 10, may be incorporated in a motion base disposed underneath the instrumented treadmill 10, such as that illustrated and described in commonly owned U.S. Pat. No. 9,081,436, the entire disclosure of which is incorporated herein by reference.

In order to accurately control the motion of the instrumented treadmill 10, a closed-loop feedback control routine may be utilized by the gait perturbation system 100. As shown in FIG. 6, the actuator control drive 27 receives the position, velocity, and torque of each actuator motor from the encoders provided as part of each actuator assembly 29. Then, from the actuator control drive 27, the position, velocity, and torque of each actuator motor is transmitted to the programmable logic controller 25, wherein the feedback control of the actuator assemblies 29 is carried out. In addition, the position, velocity, and torque of each actuator motor may also be transmitted from the actuator control drive 27 to the operator computing device 28 so that it is capable of being used to characterize the movement of the subject 42 on the instrumented treadmill 10 (e.g., the motor positional data and/or torque can be used to compute the sway of the subject).

In one or more embodiments, an emergency stop switch may be operatively coupled to the programmable logic controller 25 in order to quasi-instantaneously stop the rotation of the treadmill belts 14, 16 and/or the displacement of the instrumented treadmill 10 by the actuators 29. As such, the emergency stop switch is a safety mechanism that protects a subject disposed on the instrumented treadmill 10 from potential injury. In an exemplary embodiment, the emergency stop switch may be in the form of a red pushbutton that can be easily pressed by a user of the gait perturbation system 100 in order to stop the rotation of the treadmill belts 14, 16.

Turning to FIGS. 2 and 3, it can be seen that the instrumented treadmill 10' is similar in all respects to the instrumented treadmill 10 of FIGS. 1 and 4, except that the instrumented treadmill 10' in FIGS. 2 and 3 further includes handrails 46 attached to the base plate 12. While the subject 42 is walking or running on the instrumented treadmill 10', the handrails 46 can be grasped by the subject 42 in the event that the subject 42 loses his or her balance on the treadmill. Also, the subject 42 may grasp the handrails 46 when he or she first begins walking or running on the treadmill 10'. In addition, subjects who have balance and mobility problems may use the handrails 46 to stabilize themselves while walking or running on the treadmill 10'.

In one or more further embodiments, the gait perturbation system 100 that includes the instrumented treadmill 10 and the data acquisition/data processing device 28 further includes a body position measurement system 60 (refer to diagrammatic representation of the system in FIG. 5). The body position measurement system 60 is configured to detect the position of an upper body portion of the subject and output one or more position data signals that are representative of the position of the upper body portion of the subject. In one or more embodiments, the upper body portion of the subject is disposed above the feet of the subject. In particular, with reference to FIG. 1, the body position measurement system 60 may comprise a motion capture system having a plurality of cameras 38. In another embodiment, as shown in FIG. 4, the body position measurement system 60 may comprises a plurality of inertial measurement units (IMUs) 48 configured to be coupled to the upper body portion of the subject (e.g., as described below with regard to FIG. 4). It is to be understood that the system 100 may comprise any number or all of these body position measurement systems 38, 48 depending on the type(s) of measurements that need to be performed by the system 100.

As shown in the illustrative embodiment of FIG. 1, when the body position measurement system 60 of the gait perturbation system 100 is in the form of a motion capture system, a plurality of cameras 38 are disposed around the instrumented treadmill 10 so that the cameras 38 at least partially surround the subject 42 disposed on the treadmill 10. In the illustrative embodiment, the cameras 38 are used to track positions of a plurality of markers 40 disposed on the subject 42 as the subject moves his or her torso and limbs in 3-dimensional space. The markers on the subject 42 are used to record the position of the torso and limbs of the subject 42 in 3-dimensional space. While ten (10) cameras 38 are depicted in FIG. 1, one of ordinary skill in the art will appreciate that more or less cameras can be utilized, provided that the motion of the subject 42 is capable of being captured from substantially all angles. In the illustrative embodiment of the invention, the subject 42 has a plurality of single markers 40 applied to anatomical landmarks (e.g., the iliac spines of the pelvis, the malleoli of the ankle, and the condyles of the knee), and/or clusters of markers applied to the middle of body segments. As the subject 42 executes particular movements on the instrumented treadmill 10, the data acquisition/data processing device 28 is specially programmed to calculate the trajectory of each marker 40 in three (3) dimensions. Then, once the positional data is obtained using the motion capture system of FIG. 1, inverse kinematics may be employed in order to further determine the joint angles of the subject 42. That is, the motion capture system of FIG. 1 generates motion capture data that is representative of the captured motion of the body portions of the subject, and the data acquisition/data processing device 28 is specially programmed to determine the position of the body of the subject (i.e., limbs, torso, head, etc.) and the joint angles of the subject from the motion capture data generated by the motion capture system.

While the motion capture system of FIG. 1 described above employs a plurality of markers 40, it is to be understood that the invention is not so limited. Rather, in another embodiment of the invention, a markerless motion detection/motion capture system is utilized. The markerless motion capture system uses a plurality of high speed video cameras to record the motion of a subject without requiring any markers to be placed on the subject. Both of the aforementioned marker and markerless motion detection/motion capture systems are optical-based systems. In one embodiment, the optical motion capture system utilizes visible light, while in another alternative embodiment, the optical motion capture system employs infrared light (e.g., the system could utilize an infrared (IR) emitter to project a plurality of dots onto objects in a particular space as part of a markless motion capture system). For example, in one or more embodiments, the optical motion capture system may comprise a motion capture device with one or more cameras, one or more infrared (IR) depth sensors, and one or more microphones, which may be used to provide full-body three-dimensional (3D) motion capture, facial recognition, and voice recognition capabilities. It is also to be understood that, rather than using an optical motion detection/capture system, a suitable magnetic or electro-mechanical motion detection/capture system may also be employed to determine the position of the subject 42 on the instrumented treadmill 10.

In the illustrative embodiment, the cameras 38 depicted in FIG. 1 may be in the form of infrared-type (IR) or near infrared-type (NIR) cameras having an angular field of view range between approximately 40 degrees and approximately 80 degrees (or between 40 degrees and 80 degrees). More particularly, in one or more embodiments, the angular field of view range of the cameras 38 may be between approximately 50 degrees and approximately 70 degrees (or between 50 degrees and 70 degrees). Also, in one or more exemplary embodiments, the cameras 38 depicted in FIG. 1 may have a resolution of approximately 1.0 Megapixels, a maximum frame rate of approximately 250 feet per second (fps), and a 4 millimeter to 12 millimeter (4-12 mm) zoom lens. The cameras 38 are positioned in the gait perturbation system 100 of FIG. 1 so that each marker disposed on a subject 42 standing on the instrumented treadmill 10 is captured by at least two (2) of the cameras 38, and preferably, three (3) of the cameras 38.

Now, referring to FIG. 4, another manner in which the data acquisition/data processing device 28 may determine a position of a body portion (e.g., torso, pelvis, or head) of the subject 42 will be described. In particular, the data acquisition/data processing device 28 may also determine the position of the body portion of the subject 42 by utilizing the inertial measurement units (IMUs) 48 illustrated in FIG. 4. As shown in this figure, a subject 42 may be outfitted with a plurality of different inertial measurement units 48 for detecting motion. In the illustrative embodiment, the subject 42 is provided with two (2) inertial measurement units 48 on each of his legs (e.g., on the side or front of his legs). The subject 42 is also provided with two (2) inertial measurement units 48 on each of his arms (e.g., on the side of his arms). In addition, the subject 42 of FIG. 4 is provided with an inertial measurement unit 48 above his waist, and another inertial measurement unit 48 around his or her chest (e.g., near his sternum). In the illustrated embodiment, each of the inertial measurement units 48 is operatively coupled to the data acquisition/data processing device 28 by wireless means, such as Bluetooth, or another suitable type of personal area network wireless means.

In the illustrated embodiment of FIG. 4, each of the inertial measurement units 48 is coupled to the respective body portion of the subject 42 by a band 50. As shown in FIG. 4, each of the inertial measurement units 48 comprises an IMU housing attached to an elastic band 50. The band 50 is resilient so that it is capable of being stretched while being placed on the subject 42 (e.g., to accommodate the hand or the foot of the subject 42 before it is fitted in place on the arm or the leg of the subject 42). The band 50 can be formed from any suitable stretchable fabric, such as neoprene, spandex, and elastane. Alternatively, the band 50 could be formed from a generally non-stretchable fabric, and be provided with latching means or clasp means for allowing the band 50 to be split into two portions (e.g., the band 50 could be provided with a snap-type latching device).

In other embodiments, it is possible to attach the inertial measurement units 48 to the body portions of the subject 42 using other suitable attachment means. For example, the inertial measurement units 48 may be attached to a surface (e.g., the skin or clothing item) of the subject 42 using adhesive backing means. The adhesive backing means may comprise a removable backing member that is removed just prior to the inertial measurement unit 48 being attached to a subject 42 or object. Also, in some embodiments, the adhesive backing means may comprise a form of double-sided bonding tape that is capable of securely attaching the inertial measurement unit 48 to the subject 42 or another object.

In one or more embodiments, each inertial measurement unit 48 may comprise a triaxial (three-axis) accelerometer sensing linear acceleration $\vec{a}'$, a triaxial (three-axis) rate gyroscope sensing angular velocity $\vec{\omega}'$, a triaxial (three-axis) magnetometer sensing the magnetic north vector $\vec{n}'$, and a central control unit or microprocessor operatively coupled to each of accelerometer, gyroscope, and the magnetometer. In addition, each inertial measurement unit 48 may comprise a wireless data interface for electrically coupling the inertial measurement unit 48 to the data acquisition/data processing device 28.

Next, an illustrative manner in which the data acquisition/data processing device 28 of the gait perturbation system 100 performs the inertial measurement unit (IMU) calculations will be explained in detail. In particular, this calculation procedure will describe the manner in which the orientation and position of one or more body portions (e.g., torso or limbs) of the subject 42 could be determined using the signals from the plurality of inertial measurement units (IMUs) 48 of the motion detection system of FIG. 4. As explained above, in one or more embodiments, each inertial measurement unit 48 includes the following three triaxial sensor devices: (i) a three-axis accelerometer sensing linear acceleration $\vec{a}'$, (ii) a three-axis rate gyroscope sensing angular velocity $\vec{\omega}'$, and (iii) a three-axis magnetometer sensing the magnetic north vector $\vec{n}'$. Each inertial measurement unit 48 senses in the local (primed) frame of reference attached to the IMU itself. Because each of the sensor devices in each IMU is triaxial, the vectors $\vec{a}'$, $\vec{\omega}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the orientation $\vec{\theta}(t)$ and position $\vec{R}(t)$ in the global, unprimed, inertial frame of reference. Initially, the calculation procedure begins with a known initial orientation $\vec{\theta}_0$ and position $\vec{R}_0$ in the global frame of reference.

For the purposes of the calculation procedure, a right-handed coordinate system is assumed for both global and local frames of reference. The global frame of reference is attached to the Earth. The acceleration due to gravity is assumed to be a constant vector $\vec{g}$. Also, for the purposes of the calculations presented herein, it is presumed the sensor devices of the inertial measurement units (IMUs) provide calibrated data. In addition, all of the signals from the IMUs are treated as continuous functions of time. Although, it is to be understood the general form of the equations described herein may be readily discretized to account for IMU sensor devices that take discrete time samples from a bandwidth-limited continuous signal.

The orientation $\vec{\theta}(t)$ is obtained by single integration of the angular velocity as follows:

$$\vec{\theta}(t) = \vec{\theta}_0 + \int_0^t \vec{\omega}(t)dt \quad (2)$$

$$\vec{\theta}(t) = \vec{\theta}_0 + \int_0^t \vec{\Theta}(t)\vec{\omega}'(t)dt \quad (3)$$

where $\vec{\Theta}(t)$ is the matrix of the rotation transformation that rotates the instantaneous local frame of reference into the global frame of reference.

The position is obtained by double integration of the linear acceleration in the global reference frame. The triaxial accelerometer of each IMU senses the acceleration $\vec{a}'$ in the local reference frame. The acceleration $\vec{a}'$ has the following contributors: (i) the acceleration due to translational motion, (ii) the acceleration of gravity, and (iii) the centrifugal, Coriolis and Euler acceleration due to rotational motion. All but the first contributor has to be removed as a part of the change of reference frames. The centrifugal and Euler accelerations are zero when the acceleration measurements are taken at the origin of the local reference frame. The first integration gives the linear velocity as follows:

$$\vec{v}(t) = \vec{v}_0 + \int_0^t \{\vec{a}(t) - \vec{g}\}dt \quad (4)$$

$$\vec{v}(t) = \vec{v}_0 + \int_0^t \{\vec{\Theta}(t)[\vec{a}'(t) + 2\vec{\omega}' \times \vec{v}'(t)] - \vec{g}\}dt \quad (5)$$

where $2\vec{\omega}' \times \vec{v}'(t)$ is the Coriolis term, and where the local linear velocity is given by the following equation:

$$\vec{v}'(t) = \vec{\Theta}^{-1}(t)\vec{v}(t) \quad (6)$$

The initial velocity $\vec{v}_0$ can be taken to be zero if the motion is being measured for short periods of time in relation to the duration of Earth's rotation. The second integration gives the position as follows:

$$\vec{R}(t) = \vec{R}_0 + \int_0^t \vec{v}(t)dt \quad (7)$$

At the initial position, the IMU's local-to-global rotation's matrix has an initial value $\vec{\Theta}(0) = \vec{\Theta}_0$. This value can be derived by knowing the local and global values of both the magnetic north vector and the acceleration of gravity. Those two vectors are usually non-parallel. This is the requirement for the $\vec{\Theta}_0(\vec{g}', \vec{n}', \vec{g}, \vec{n})$ to be unique. The knowledge of either of those vectors in isolation gives a family of non-unique solutions $\vec{\Theta}_0(\vec{g}', \vec{g})$ or $\vec{\Theta}_0(\vec{n}', \vec{n})$ that are unconstrained in one component of rotation. The $\vec{\Theta}_0(\vec{g}', \vec{n}', \vec{g}, \vec{n})$ has many implementations, with the common one being the Kabsch algorithm. As such, using the calculation procedure described above, the data acquisition/data processing device 28 of the gait perturbation system 100 may determine the orientation $\vec{\theta}(t)$ and position $\vec{R}(t)$ of one or more body portions of the subject 42. For example, the orientation of a limb of the subject 42 (e.g., the right arm of the subject 42 in FIG. 4) may be determined by computing the orientation $\vec{\theta}(t)$ and position $\vec{R}(t)$ of two points on the limb of the subject 42 (i.e., at the respective locations of two inertial measurement units (IMUs) 48 disposed on the limb of the subject 42).

As explained above, the inertial measurement units (IMUs) 48 of FIG. 4 sense measured quantities (i.e., acceleration, angular velocity) that are representative of the position of the body portion of the subject 42 and output a plurality of position data signals that are representative of the position of the body portion of the subject 42. The data acquisition/data processing device 28 is specially programmed to determine the position of the body portion of the subject 42 using the plurality of position data signals that are output by the plurality of inertial measurement units 48 (e.g., the plurality of position data signals from the inertial measurement units 48 may be used to determine the position of the subject 42 relative to the center of the treadmill belts 14, 16 or to approximate the subject's center-of-gravity along the y-axis).

Now, the manner in which the programmable logic controller 25 and data acquisition/data processing device 28 of the gait perturbation system 100 are specially programmed to perturb the gait of the subject 42 disposed on the instrumented treadmill 10 will be described. As explained above, the data acquisition/data processing device 28 is operatively coupled to the programmable logic controller 25 of the instrumented treadmill 10. In one illustrative embodiment, the programmable logic controller 25 (i.e., a data processing device) is specially programmed to generate a first base velocity signal for controlling the speed of the treadmill belts 14, 16 of the instrumented treadmill 10 and a second velocity signal for introducing a perturbation to the treadmill belts 14, 16. Also, in the illustrative embodiment, programmable logic controller 25 is specially programmed to combine the first base velocity signal with the second velocity signal to form a composite velocity signal, and to control the speed set points of the treadmill belts 14, 16 using the composite velocity signal such that the treadmill belts 14, 16 perturb a gait of the person. As described in detail hereinafter, in order to create perturbations, the frequency and the amplitude of the treadmill belt speed can be varied. In an alternative illustrative embodiment, the data acquisition/data processing device 28, rather than the programmable logic controller 25, may be specially programmed to generate the first base velocity signal for controlling the speed of the treadmill belts 14, 16 of the instrumented treadmill 10, to generate the second velocity signal for introducing a perturbation to the treadmill belts 14, 16, and to combine the first base velocity signal and the second velocity signal to form the composite velocity signal.

Figure 7:
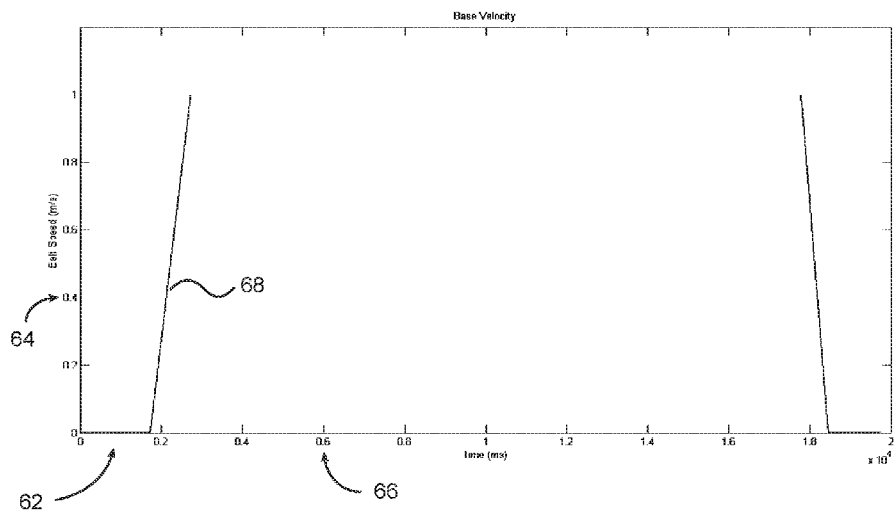
FIG. 7 is a graph illustrating a base velocity signal with no perturbations for controlling the speed set point of the one or more treadmill belts of the instrumented treadmill of FIG. 1.

An exemplary base velocity signal generated by the programmable logic controller 25 or the data acquisition/data processing device 28 for controlling the speed of the treadmill belts 14, 16 of the instrumented treadmill 10 is illustrated in the graph 62 of FIG. 7. As shown in this figure, the y-axis 64 of the graph 62 is the treadmill belt speed in meters per second (m/s), while the x-axis 66 of the graph 62 is the time in milliseconds (ms). In the graph 62 of FIG. 7, it can be seen that the base velocity curve 68 ramps up to 1.0 meters per second at approximately 2,000 milliseconds and then ramps down back to zero at approximately 18,000 milliseconds. In FIG. 7, no perturbations have been applied to the treadmill belts 14, 16.

In the illustrative embodiment, the second velocity signal for introducing a perturbation to the treadmill belts 14, 16 comprises a stochastic signal, and the programmable logic controller 25 or the data acquisition/data processing device 28 is specially programmed to add the stochastic signal to the base velocity signal so as to make the treadmill belts 14, 16 oscillate while the subject 42 is disposed thereon. As will be described hereinafter, the stochastic signal may be of uniform or normal distribution. As such, the stochastic signal is capable of simulating uneven terrain or slips and falls while the subject 42 is walking or running on the instrumented treadmill 10.

Figure 8:
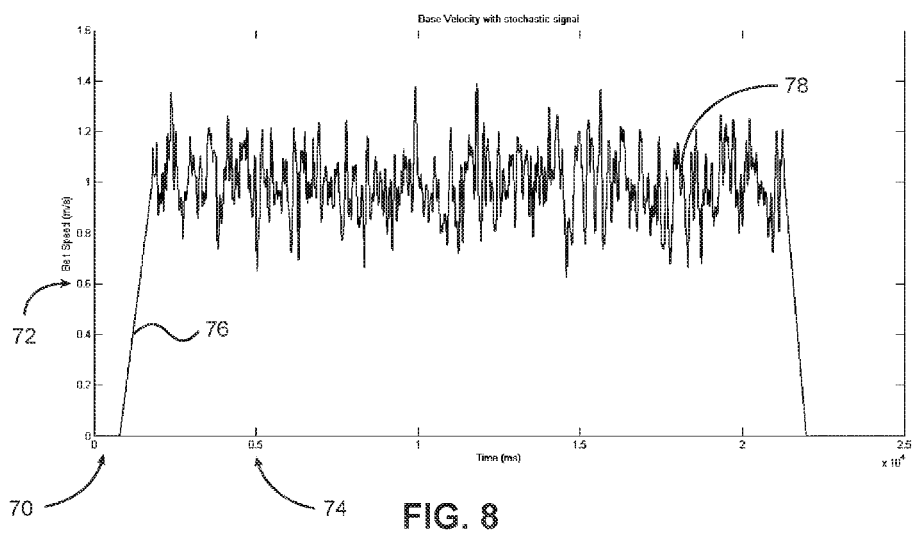
FIG. 8 is a graph illustrating a combined base velocity and stochastic signal for controlling the speed set point of the one or more treadmill belts of the instrumented treadmill of FIG. 1.

An exemplary combined base velocity and stochastic signal generated by the programmable logic controller 25 or the data acquisition/data processing device 28 for controlling the speed of the treadmill belts 14, 16 of the instrumented treadmill 10 is illustrated in the graph 70 of FIG. 8. As shown in this figure, the y-axis 72 of the graph 70 is the treadmill belt speed in meters per second (m/s), while the x-axis 74 of the graph 70 is the time in milliseconds (ms). In the graph 70 of FIG. 8, it can be seen that the combined base velocity/stochastic signal curve comprises a base velocity curve portion 76 and stochastic signal curve portion 78. The base velocity curve portion 76 ramps up to 1.0 meters per second at approximately 2,000 milliseconds and then ramps down back to zero at approximately 22,000 milliseconds. In FIG. 8, the stochastic signal is added to the base velocity signal of 1.0 meters per second. As shown in FIG. 8, the combined base velocity and stochastic signal generated by the programmable logic controller 25 or the data acquisition/data processing device 28 is never negative, so the belts 14, 16 of the instrumented treadmill do not undergo a change in their rotational directions over time (i.e., because the velocity is always a positive value, the direction of the belts 14, 16 is not reversed in the exemplary signal of FIG. 8). As shown in FIG. 8, the amplitude of the stochastic signal curve portion 78 is randomly changing over time (i.e., the amplitude consistently changes over time in a random manner). Similarly, the frequency of the stochastic signal curve portion 78 is randomly changing over time (i.e., the frequency consistently changes over time in a random manner). Thus, advantageously, the programmable logic controller 25 or the data acquisition/data processing device 28 generates a stochastic signal with both a randomly varying amplitude and frequency that results in a random perturbation being delivered to the subject 42 on the instrumented treadmill 10. The manner of delivery of the perturbation to the subject 42 on the treadmill 10 is not just random, but rather the stochastic signal itself controlling the perturbation has both random amplitude and frequency content. Advantageously, the belt speed of the instrumented treadmill 10 does not have a constant slope that can be learned by the subject 42 over time. The stochastic signal generated by the programmable logic controller 25 or the data acquisition/data processing device 28 significantly changes the functionality of the instrumented treadmill 10 by enabling the instrumented treadmill 10 to simulate unexpected, real-life scenarios that could be encountered by the subject 42, such as slip and fall events. As such, controlling the treadmill 10 using the stochastic signal enables the instrumented treadmill 10 to model real-life conditions encountered by the subject 42 so that the testing and/or training of the subject 42 using the treadmill 10 may be greatly enhanced.

In the illustrative embodiment, the generation of the combined base velocity and stochastic signal by the programmable logic controller 25 or the data acquisition/data processing device 28 comprises a plurality of different steps. Initially, by utilizing the input devices 32, 36 of the data acquisition/data processing device 28 (e.g., the keyboard 32 and/or touchpad 36), a user enters the following input values: (i) the stochastic signal base amplitude, (ii) a frequency of the stochastic signal (i.e., the cut-off frequency of the stochastic signal), and (iii) a signal type of the stochastic signal (i.e., uniform or random). Then, the programmable logic controller 25 or the data acquisition/data processing device 28 generates the random or uniform stochastic signal based upon the amplitude and frequency values entered by the user. The amplitude value entered by the user determines the upper and lower bounds of the stochastic signal generated by the programmable logic controller 25 or the data acquisition/data processing device 28, while the cut-off frequency value entered by the user determines the upper frequency limit of the stochastic signal generated by the programmable logic controller 25 or the data acquisition/data processing device 28. Finally, the programmable logic controller 25 updates belt speed set point(s) of the treadmill belts 14, 16 of the instrumented treadmill 10. Each of these steps will be described in further detail hereinafter. Referring to FIG. 6, when the programmable logic controller 25 generates the stochastic signal, the base amplitude, the cut-off frequency, and the signal type of the stochastic signal are transmitted from the data acquisition/data processing device 28 to the programmable logic controller 25 so that the stochastic signal is able to be generated by the programmable logic controller 25.

In the illustrative embodiment, the user may be permitted to enter a stochastic amplitude value in the range between zero and approximately 2.0 meters, inclusive (or between zero and 2.0 meters, inclusive). If the user enters different amplitude values for each of the treadmill belts 14, 16, the difference in the two amplitude values may not exceed 1.0 meter in the illustrative embodiment. Similarly, in the illustrative embodiment, the user may be permitted to enter a cut-off frequency value in the range between zero and approximately 10 Hertz, inclusive (or between zero and 10 Hertz, inclusive). If the user enters different cut-off frequency values for each of the treadmill belts 14, 16, the difference in the cut-off frequency values may not exceed 5 Hertz in the illustrative embodiment. Also, in the illustrative embodiment, the amplitude has to be less than the base velocity (e.g., if the base velocity is 2.0 meters per second, then the amplitude needs to be less than 2.0 meters). In general, a low amplitude would simulate vibrations, while a high amplitude would imitate a slip condition.

In addition to entering the amplitude, cut-off frequency, and signal type of the stochastic signal, the user is also able to selectively regulate the beginning and end of the stochastic signal by pressing a graphical start button on the operator display 34 to initiate the stochastic signal, and then by subsequently pressing a graphical stop button on the operator display 34 to end the stochastic signal (i.e., when the display is a touchscreen).

Figure 9:
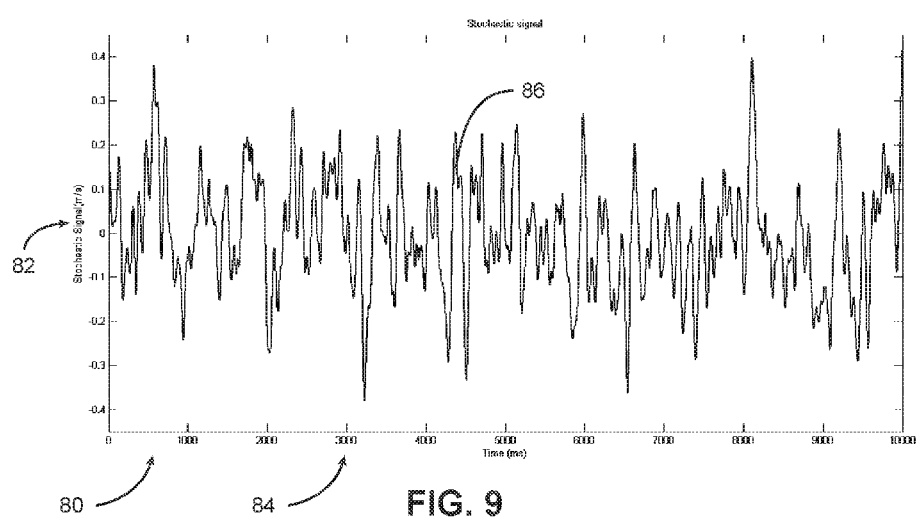
FIG. 9 is a graph illustrating a uniform stochastic signal with a base amplitude of 0.9 meters and a cutoff frequency of 5 Hertz.
Figure 10:
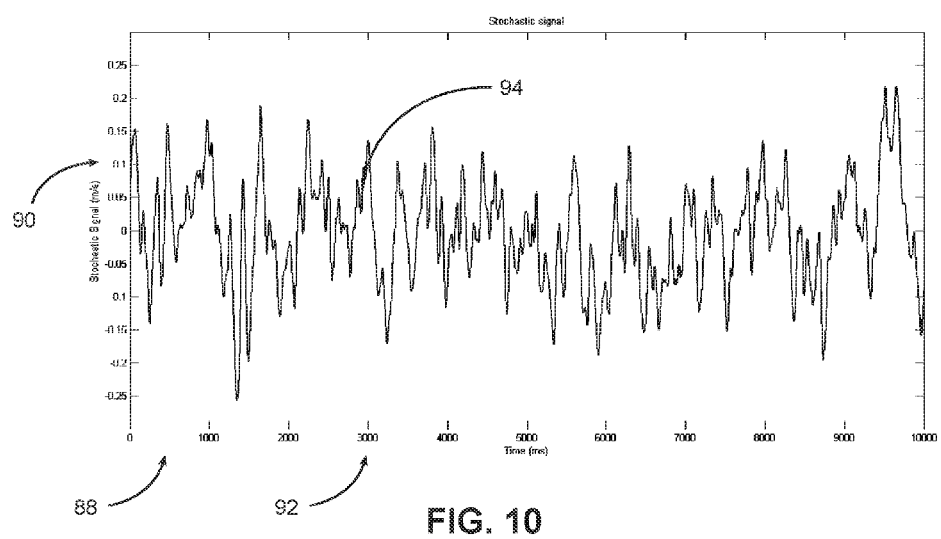
FIG. 10 is a graph illustrating a uniform stochastic signal with a base amplitude of 0.5 meters and a cutoff frequency of 5 Hertz.

In the illustrative embodiment, the belt speed of each belt 14, 16 of the instrumented dual belt treadmill 10 is capable of being updated independently. In the initial step of the process, as explained above, the user is allowed to input the amplitude of the stochastic signal, the frequency of the stochastic signal, and the stochastic signal type (i.e., either uniform or normal). The base amplitude that is input for the signal determines the range of the stochastic signal that is generated by the programmable logic controller 25 or the data acquisition/data processing device 28. For example, a first exemplary uniform stochastic signal generated by the programmable logic controller 25 or the data acquisition/data processing device 28 is illustrated in the graph 80 of FIG. 9. As shown in this figure, the y-axis 82 of the graph 80 is speed in meters per second (m/s), while the x-axis 84 of the graph 80 is the time in milliseconds (ms). The uniform stochastic signal curve 86 in FIG. 9 has a base amplitude of 0.9 meters and a cut-off frequency of 5 Hertz. In the graph 80 of FIG. 9, it can be seen that the uniform stochastic signal curve 86 oscillates between a minimum lower limit of approximately −0.40 meters per second and a maximum upper limit of approximately 0.40 meters per second over a time duration of approximately 10,000 milliseconds. As another example, a second exemplary uniform stochastic signal generated by the programmable logic controller 25 or the data acquisition/data processing device 28 is illustrated in the graph 88 of FIG. 10. As shown in this figure, the y-axis 90 of the graph 88 is speed in meters per second (m/s), while the x-axis 92 of the graph 88 is the time in milliseconds (ms). The uniform stochastic signal curve 94 in FIG. 10 has a base amplitude of 0.5 meters and a cut-off frequency of 5 Hertz. In the graph 88 of FIG. 10, it can be seen that the uniform stochastic signal curve 94 oscillates between a minimum lower limit of approximately −0.25 meters per second and a maximum upper limit of approximately 0.225 meters per second over a time duration of approximately 10,000 milliseconds.

Figure 11:
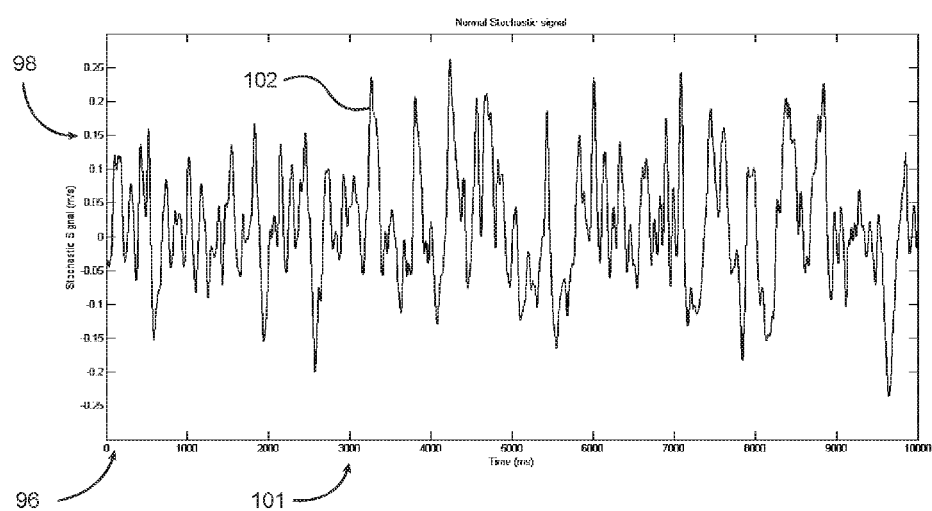
FIG. 11 is a graph illustrating a normal stochastic signal with a base amplitude of 0.9 meters and a cutoff frequency of 5 Hertz.
Figure 12:
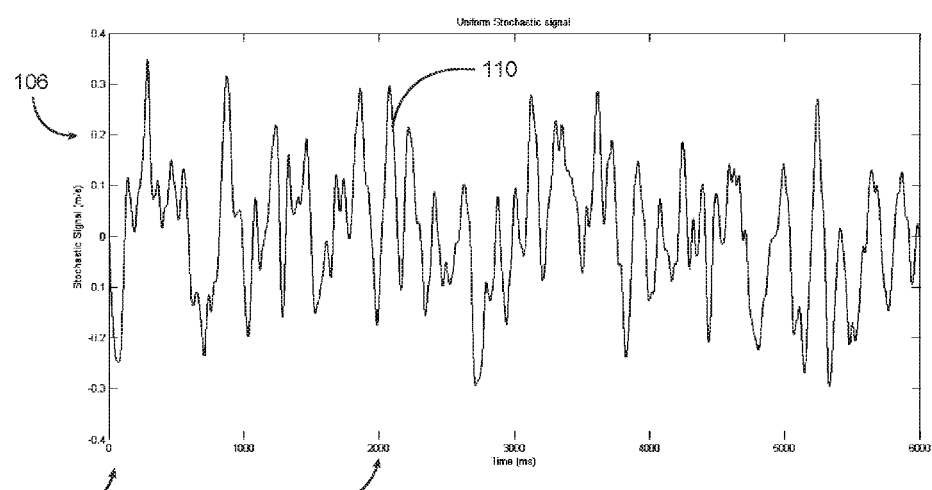
FIG. 12 is a graph illustrating a uniform stochastic signal with a base amplitude of 0.9 meters and a cutoff frequency of 10 Hertz.

As yet another example of a perturbation input signal, an exemplary normal stochastic signal generated by the programmable logic controller 25 or the data acquisition/data processing device 28 is illustrated in the graph 96 of FIG. 11. As shown in this figure, the y-axis 98 of the graph 96 is speed in meters per second (m/s), while the x-axis 101 of the graph 96 is the time in milliseconds (ms). The normal stochastic signal curve 102 in FIG. 11 has a base amplitude of 0.9 meters and a cut-off frequency of 5 Hertz. In the graph 96 of FIG. 11, it can be seen that the normal stochastic signal curve 102 oscillates between a minimum lower limit of approximately −0.25 meters per second and a maximum upper limit of approximately 0.25 meters per second over a time duration of approximately 10,000 milliseconds. As still another example, a third exemplary uniform stochastic signal generated by the programmable logic controller 25 or the data acquisition/data processing device 28 is illustrated in the graph 104 of FIG. 12. As shown in this figure, the y-axis 106 of the graph 104 is speed in meters per second (m/s), while the x-axis 108 of the graph 104 is the time in milliseconds (ms). The uniform stochastic signal curve 110 in FIG. 12 has a base amplitude of 0.9 meters and a cut-off frequency of 10 Hertz. In the graph 104 of FIG. 12, it can be seen that the uniform stochastic signal curve 110 oscillates between a minimum lower limit of approximately −0.30 meters per second and a maximum upper limit of approximately 0.36 meters per second over a time duration of approximately 6,000 milliseconds.

In the second step of the process, where a random uniform or normal random signal is generated by the programmable logic controller 25 or the data acquisition/data processing device 28 at the selected cut-off frequency, a random number function or subroutine may be used to generate the uniform signal random numbers (e.g., the DRAND function block in a TwinCAT software package). In the illustrative embodiment, the random number function utilized by the programmable logic controller 25 or the data acquisition/data processing device 28 requires an initial value input for the specification of the random number series. The output returns a pseudo-random number in the range −1.0 to 1.0 with double accuracy. That is, the random number function generates the same sequence of random numbers each time that the same seed is utilized. As such, in an exemplary embodiment, the seed value that is used for the random number function is acquired for each trial from the low DW of the system time, which gives a sufficiently random seed for each trial. That way, the programmable logic controller 25 or the data acquisition/data processing device 28 does not generate the same random number sequence or produce any other perturbation trends from trial to trial. In one or more embodiments, the operating system time stamp is a 64-bit integer value, with a precision of 100 nanoseconds (ns), which is updated with every call of the programmable logic controller (PLC) 25. In one or more embodiments, the low DW (timeLoDW) is the low-value 4 bytes of the time stamp and it changes very rapidly at rate of 0.01 milliseconds (ms). The random signal has a varying frequency. The randomness of the stochastic signal is highly advantageous because the subjects being tested on the instrumented treadmill 10 are not able to as easily learn how to overcome a slip-and-fall perturbation during a testing or training routine. If the perturbation employed was always the same, then eventually subjects would learn how to adapt to the perturbation, and the training would become less effective.

Figure 13:
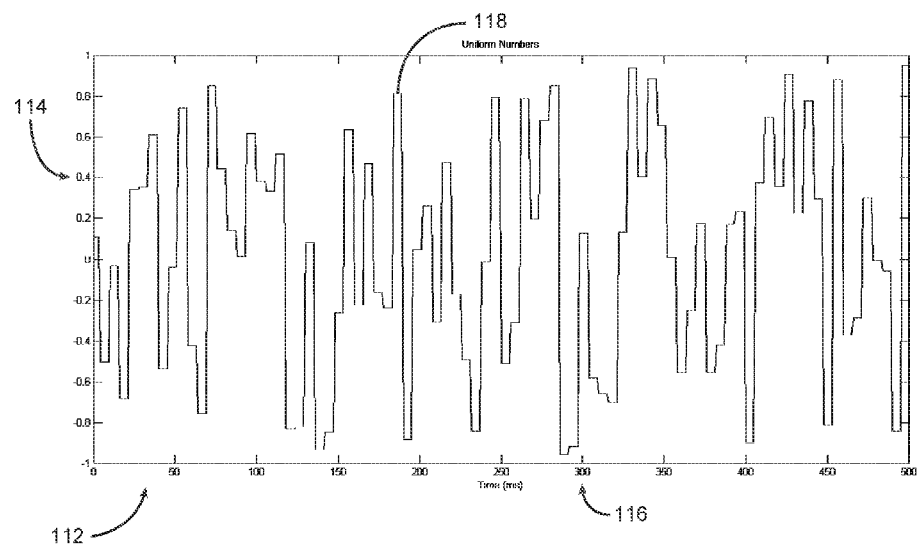
FIG. 13 is a graph illustrating a uniform random numbers curve generated by the data processing device of the gait perturbation system.

An exemplary uniform random numbers curve generated by the programmable logic controller 25 or data acquisition/data processing device 28 using a random number function or subroutine (e.g., DRAND function block) is illustrated in the graph 112 of FIG. 13. As shown in this figure, the y-axis 114 of the graph 112 is the random number value (dimensionless), while the x-axis 116 of the graph 112 is the time in milliseconds (ms). In the graph 112 of FIG. 13, it can be seen that the uniform random numbers curve 118 comprises a plurality of random number values between a lower limit value of approximately −0.95 and an upper limit value of approximately 0.90.

When the user selects a uniform-type stochastic signal, a uniform random numbers curve, such as that depicted in FIG. 13, is used for controlling the speed set points of the belts 14, 16 of the instrumented dual belt treadmill 10. However, if the user alternatively selects a normal-type stochastic signal, two (2) uniform signals U1 and U2 generated using the random number function are converted into normal signal N using the following Box-Muller transform equation:

$$N=\sqrt{-2\ln U1}\,\cos(2\pi U2) \quad (8)$$

Figure 14:
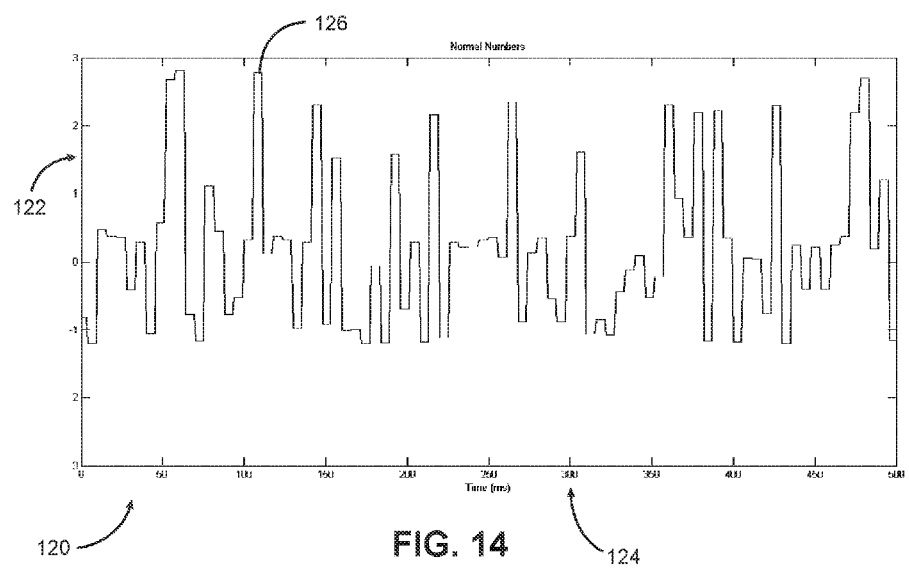
FIG. 14 is a graph illustrating a normal random numbers curve generated by the data processing device of the gait perturbation system.

An exemplary normal random numbers curve generated by the programmable logic controller 25 or the data acquisition/data processing device 28 using equation (8) to perform a Box-Muller transformation is illustrated in the graph 120 of FIG. 14. As shown in this figure, the y-axis 122 of the graph 120 is the random number value (dimensionless), while the x-axis 124 of the graph 120 is the time in milliseconds (ms). In the graph 120 of FIG. 14, it can be seen that the normal random numbers curve 126 comprises a plurality of random number values between a lower limit value of approximately −1.2 and an upper limit value of approximately 2.8. The random variables illustrated in FIG. 14 are generated in the interval [3,−3].

Figure 15:
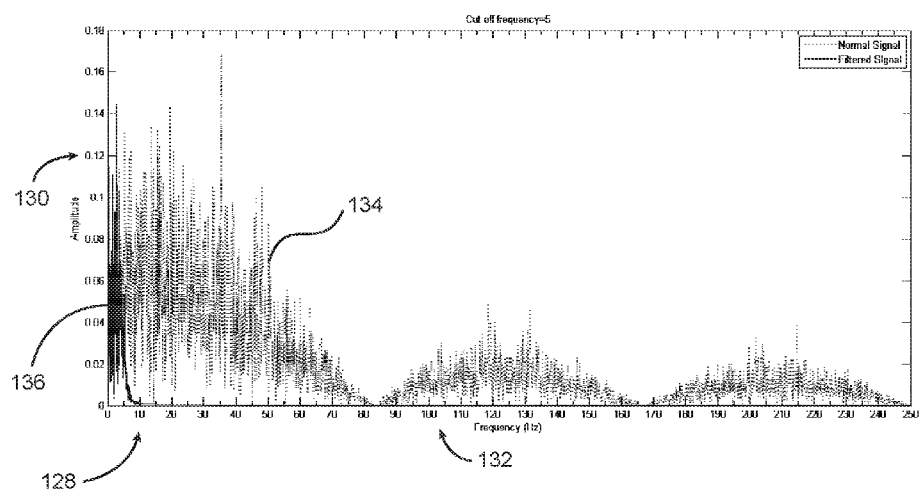
FIG. 15 is a graph illustrating a normal signal curve and filtered data curve at a cut-off frequency of 5 Hertz.
Figure 16:
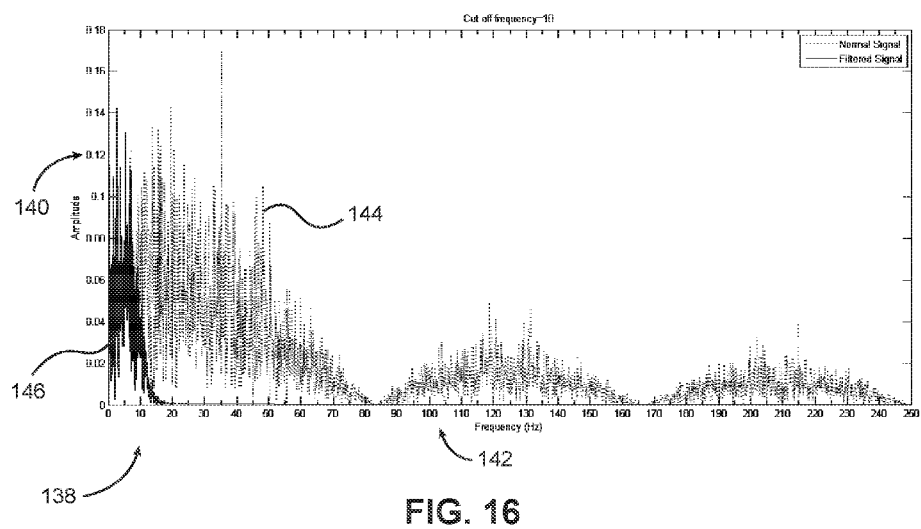
FIG. 16 is a graph illustrating a normal signal curve and filtered data curve at a cut-off frequency of 10 Hertz.

In the illustrative embodiment, the uniform or normal signal is then passed through a fourth order low pass Butterworth filter to limit the frequency component of the signal at a user specified value (i.e., at the frequency entered by the user). For example, a first exemplary filtered signal generated by the programmable logic controller 25 or the data acquisition/data processing device 28 is illustrated in the graph 128 of FIG. 15. As shown in this figure, the y-axis 130 of the graph 128 is the amplitude value of the signal (dimensionless), while the x-axis 132 of the graph 128 is the frequency of the signal in Hertz (Hz). In the graph 128 of FIG. 15, the unfiltered normal signal curve 134 is indicated using a dashed line, while the filtered normal signal curve 136 is indicated using a solid line. In FIG. 15, a cut-off frequency of 5 Hertz is used in order to generally filter out the frequency content of the normal signal curve 134 which has a frequency of greater than 5 Hertz. As such, the frequency content of the normal signal curve used for controlling the perturbation of the instrumented treadmill 10 is generally limited to the user-specified frequency of 5 Hertz in FIG. 15. As another example, a second exemplary filtered signal generated by the programmable logic controller 25 or the data acquisition/data processing device 28 is illustrated in the graph 138 of FIG. 16. As shown in this figure, the y-axis 140 of the graph 138 is the amplitude value of the signal (dimensionless), while the x-axis 142 of the graph 138 is the frequency of the signal in Hertz (Hz). In the graph 138 of FIG. 16, the unfiltered normal signal curve 144 is indicated using a dashed line, while the filtered normal signal curve 146 is indicated using a solid line. In FIG. 16, a cut-off frequency of 10 Hertz is used in order to generally filter out the frequency content of the normal signal curve 144 which has a frequency of greater than 10 Hertz. As such, the frequency content of the normal signal curve used for controlling the perturbation of the instrumented treadmill 10 is generally limited to the user-specified frequency of 10 Hertz in FIG. 16.

Figure 17:
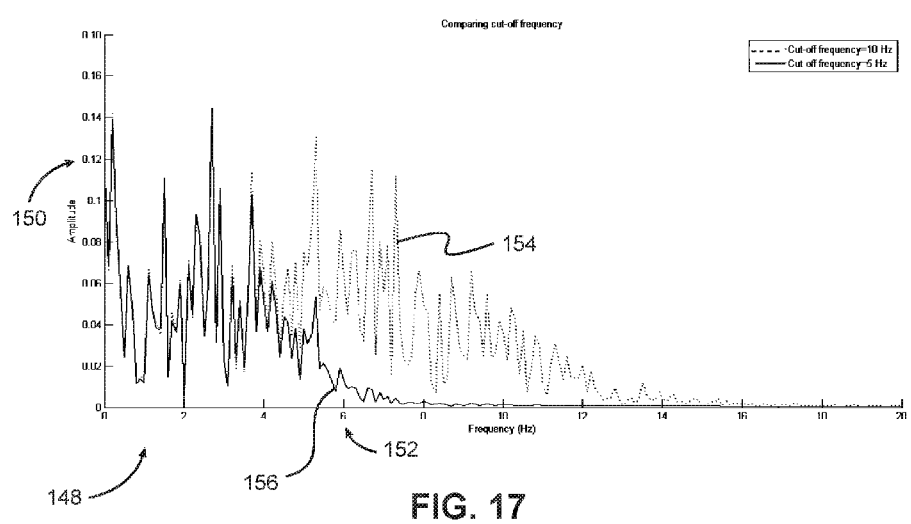
FIG. 17 is a graph comparing filtered data curves with cut-off frequencies of 5 Hertz and 10 Hertz.

Turning to FIG. 17, it can be seen that a graph 148 comparing the filtered data with cut-off frequencies of 5 Hertz and 10 Hertz is illustrated therein. Similar to FIGS. 15 and 16 described above, the y-axis 150 of the graph 148 depicted in FIG. 17 is the amplitude value of the signal (dimensionless), while the x-axis 152 of the graph 148 is the frequency of the signal in Hertz (Hz). In the graph 148 of FIG. 17, the filtered data curve 156 with a cut-off frequency of 5 Hertz is indicated using a solid line, while the filtered data curve 154 with a cut-off frequency of 10 Hertz is indicated using a dashed line.

In the illustrative embodiment, prior to the third step of the process, where the programmable logic controller 25 or the data acquisition/data processing device 28 updates belt speed set point(s) of the treadmill belts 14, 16 of the instrumented treadmill 10, the filtered signal is multiplied by the user-specified amplitude value so as to generate the stochastic signal for updating the belt speed set point(s). When the uniform-type stochastic signal is selected by the user, the uniform stochastic signal for updating the belt speed set point(s) is determined by the programmable logic controller 25 or the data acquisition/data processing device 28 in accordance with the following equation:

Uniform stochastic signal=filtered uniform signal*Amplitude  (9)

Thus, in accordance with equation (9) above, the uniform stochastic signal is a function of the filtered, randomly-generated uniform signal and the user-specified amplitude value. More specifically, the programmable logic controller 25 or the data acquisition/data processing device 28 determines the uniform stochastic signal by computing the multiplicative product between the filtered uniform signal and the user-specified amplitude value. Alternatively, when the normal-type stochastic signal is selected by the user, the normal stochastic signal for updating the belt speed set point(s) is determined by the programmable logic controller 25 or the data acquisition/data processing device 28 in accordance with the following equation:

Normal stochastic signal=filtered normal signal*Amplitude/3  (10)

Thus, in accordance with equation (10) above, the normal stochastic signal is a function of the filtered, normalized randomly-generated uniform signal and the user-specified amplitude value. More specifically, the programmable logic controller 25 or the data acquisition/data processing device 28 determines the normal stochastic signal by computing the multiplicative product between the filtered normal signal and one-third of the user-specified amplitude value.

In one or more embodiments, the aforedescribed belt speed calculations are specially programmed on an embedded computer (e.g., the programmable logic controller 25 or the data acquisition/data processing device 28) that provides a deterministic program cycle time of 1 milliseconds (ms). In other words, the belt speed update rate of 1 kilohertz (kHz) is guaranteed by either the hardware architecture of the embedded computer or a real-time operating system (e.g., firmware) that runs on it. In these one or more embodiments, the updated belt speed set points are sent to a servo controller (i.e., actuator control drive 27), which controls the belt motor speed with a closed-loop rate of 4 kilohertz (kHz). In these one or more embodiments, the firmware of the instrumented treadmill 10 controls the treadmill belt perturbations.

In the illustrative embodiment, the programmable logic controller 25 or the data acquisition/data processing device 28 may be specially programmed so as to enable the belts 14, 16 of the instrumented treadmill 10 to be controlled in two different modes: (i) a dual stochastic mode, and (ii) independent left/right stochastic mode. In the dual stochastic mode, the programmable logic controller 25 or the data acquisition/data processing device 28 controls the speed set point of each of the treadmill belts 14, 16 using the same combined base velocity and stochastic signal so that the belts 14, 16 rotate together in unison. In the independent left/right stochastic mode, the programmable logic controller 25 or the data acquisition/data processing device 28 controls the speed set point of each of the treadmill belts 14, 16 using different combined base velocity and stochastic signals so that the belts 14, 16 do not rotate together (i.e., the belt speed set point of the left belt 14 is controlled independently from the belt speed set point of the right belt 16).

In a further embodiment, the programmable logic controller 25 or the data acquisition/data processing device 28 may be specially programmed to additionally control the belts 14, 16 of the instrumented treadmill 10 in a pulsed mode of operation. In the pulsed operation mode, the belts 14, 16 of the instrumented treadmill 10 are displaced from an initial stationary position (i.e., the belts 14, 16 undergo pure translation from a standstill position). In the pulsed mode of operation, the maximum pulse distance may be approximately 1.25 meters (or 1.25 m), the maximum pulse velocity may be approximately 6.5 meters per second (or 6.5 m/s), the maximum pulse acceleration may be approximately 10.0 meters per second squared (or 10 m/s$^2$), the maximum pulse deceleration may be approximately 10.0 meters per second squared (or 10 m/s$^2$), the maximum difference in the pulse distance between the treadmill belts 14, 16 may be approximately 1.0 meter (or 1 m), the maximum difference in the pulse velocity between the treadmill belts 14, 16 may be approximately 5.5 meters per second (or 5.5 m/s), the maximum difference in the pulse acceleration between the treadmill belts 14, 16 may be approximately 9.0 meters per second squared (or 9.0 m/s$^2$), and the maximum difference in the pulse deceleration between the treadmill belts 14, 16 may be approximately 9.0 meters per second squared (or 9.0 m/s$^2$).

It is readily apparent from the above detailed description that the gait perturbation system 100 significantly advances the field of human balance assessment and human gait analysis. For example, the gait perturbation system 100 is capable of simulating real-life conditions by subjecting the person being tested to dynamic instability by controlling the treadmill belt speed based upon the stochastic signal generated by the programmable logic controller 25 or the data acquisition/data processing device 28. As another example, the aforedescribed gait perturbation system 100 is capable of generating random stimuli (e.g., randomly regulating the treadmill belt speed) in order to emulate real-life conditions encountered by the person undergoing testing. As yet another example, the gait perturbation system 100 described above is capable of more effectively training a person with a gait disorder by delivering random stimuli (e.g., randomly regulating the treadmill belt speed) to the person so that he or she is able to more effectively react to unpredictable disturbances that are encountered in real-life scenarios.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A gait perturbation system comprising, in combination:
a gait perturbation device configured to receive a person thereon, the gait perturbation device including:
one or more displaceable components configured to be displaced at a plurality of different speeds, the one or more displaceable components having one or more respective surfaces for receiving one or more respective limbs of the person; and
one or more speed adjustment mechanisms coupled to the one or more displaceable components, the one or more speed adjustment mechanisms configured to adjust the speed set point at which the one or more displaceable components are displaced, the one or more speed adjustment mechanisms being primary means for displacing the one or more displaceable components; and
a data processing device operatively coupled to the one or more speed adjustment mechanisms, the data processing device configured to generate a first base velocity signal for controlling the speed of the one or more displaceable components during a time period beginning with a starting time and concluding with an ending time and generate a second velocity signal for introducing a perturbation to the one or more displaceable components during the time period beginning with the starting time and concluding with the ending time, the second velocity signal generated by the data processing device being in the form of a stochastic signal, the data processing device further configured to combine the first base velocity signal with the second stochastic velocity signal to form a composite velocity signal during the time period beginning with the starting time and concluding with the ending time, and to control the speed set point of the one or more displaceable components using the composite velocity signal such that the one or more displaceable components perturb a gait of the person.

2. The gait perturbation system according to claim 1, wherein the gait perturbation device comprises a treadmill, and the one or more displaceable components comprise one or more belts of the treadmill; and wherein the one or more speed adjustment mechanisms are configured to adjust the speed set point at which the one or more belts of the treadmill are rotated.

3. The gait perturbation system according to claim 2, wherein the treadmill comprises an instrumented treadmill, the instrumented treadmill including at least one force transducer, the at least one force transducer configured to sense one or more measured quantities and output one or more signals that are representative of one or more loads being applied to the one or more respective surfaces of the one or more belts of the treadmill by the person.

4. The gait perturbation system according to claim 2, wherein the one or more speed adjustment mechanisms comprise one or more servo controllers configured to adjust the speed set point at which the one or more belts of the treadmill are rotated.

5. The gait perturbation system according to claim 1, wherein the second stochastic velocity signal comprises one of: (i) a uniform stochastic signal and (ii) a normal stochastic signal.

6. The gait perturbation system according to claim 1, further comprising at least one input device, the at least one input device configured to enable a user to manually input at least one of: (i) an amplitude of the second stochastic velocity signal, (ii) a frequency of the second stochastic velocity signal, and (iii) a signal type of the second stochastic velocity signal, the signal type of the second stochastic velocity signal being selected from the group consisting of a uniform stochastic signal and a random stochastic signal.

7. The gait perturbation system according to claim 6, wherein the data processing device is configured to generate the second stochastic velocity signal based upon at least one of: (i) the amplitude of the second stochastic velocity signal input by the user, (ii) the frequency of the second stochastic velocity signal input by the user, and (iii) the signal type of the second stochastic velocity signal input by the user.

8. The gait perturbation system according to claim 7, wherein the data processing device is configured to generate the second stochastic velocity signal based upon the amplitude of the second stochastic velocity signal input by the user, and at least one of: (i) the frequency of the second stochastic velocity signal input by the user, and (ii) the signal type of the second stochastic velocity signal input by the user.

9. The gait perturbation system according to claim 8, wherein the second stochastic velocity signal comprises a uniform stochastic signal, the data processing device configured to compute the uniform stochastic signal as a function of a randomly generated uniform signal and the amplitude input by the user.

10. The gait perturbation system according to claim 8, wherein the second stochastic velocity signal comprises a normal stochastic signal, the data processing device configured to compute the normal stochastic signal as a function of a normalized randomly generated uniform signal and the amplitude input by the user.

11. The gait perturbation system according to claim 1, further comprising secondary means for displacing the one or more displaceable components of the gait perturbation device in a direction different from a primary direction of displacement of the one or more displaceable components, the secondary means for displacing the one or more displaceable components of the gait perturbation device being operatively coupled to the data processing device; and wherein the data processing device is configured to generate a translation perturbation signal and to output the translation perturbation signal to the secondary means for displacing the one or more displaceable components of the gait perturbation device so that the one or more displaceable components of the gait perturbation device are displaced in a direction different from a primary direction of displacement of the one or more displaceable components.

12. A gait perturbation system comprising, in combination:

a gait perturbation device configured to receive a person thereon, the gait perturbation device including:
one or more displaceable components configured to be displaced at a plurality of different speeds, the one or more displaceable components having one or more respective surfaces for receiving one or more respective limbs of the person; and
one or more speed adjustment mechanisms coupled to the one or more displaceable components, the one or more speed adjustment mechanisms configured to adjust the speed set point at which the one or more displaceable components are displaced; and a data processing device operatively coupled to the one or more speed adjustment mechanisms, the data processing device configured to generate a stochastic signal for introducing a perturbation to the one or more displaceable components, the stochastic signal oscillating above and below a base velocity signal, and the data processing device further configured to control the speed set point of the one or more displaceable components using the stochastic signal such that the one or more displaceable components perturb a gait of the person.

13. The gait perturbation system according to claim 12, wherein the gait perturbation device comprises a treadmill, and the one or more displaceable components comprise one or more belts of the treadmill; and wherein the one or more speed adjustment mechanisms are configured to adjust the speed set point at which the one or more belts of the treadmill are rotated.

14. The gait perturbation system according to claim 13, wherein the treadmill comprises an instrumented treadmill, the instrumented treadmill including at least one force transducer, the at least one force transducer configured to sense one or more measured quantities and output one or more signals that are representative of one or more loads being applied to the one or more respective surfaces of the one or more belts of the treadmill by the person.

15. The gait perturbation system according to claim 13, wherein the one or more speed adjustment mechanisms comprise one or more servo controllers configured to adjust the speed set point at which the one or more belts of the treadmill are rotated.

16. The gait perturbation system according to claim 12, wherein the stochastic signal generated by the data processing device comprises a uniform stochastic signal, the data processing device configured to compute the uniform stochastic signal as a function of a randomly generated uniform signal and an amplitude value input by a user using an input device operatively coupled to the data processing device.

17. The gait perturbation system according to claim 12, wherein the stochastic signal generated by the data processing device comprises a normal stochastic signal, the data processing device configured to compute the normal stochastic signal as a function of a normalized randomly generated uniform signal and an amplitude value input by a user using an input device operatively coupled to the data processing device.

18. A method for testing and/or training a person using a gait perturbation system, the method comprising the steps of:
   providing a gait perturbation device configured to receive a person thereon, the gait perturbation device including:
      one or more displaceable components configured to be displaced at a plurality of different speeds, the one or more displaceable components having one or more respective surfaces for receiving one or more respective limbs of the person; and
      one or more speed adjustment mechanisms coupled to the one or more displaceable components, the one or more speed adjustment mechanisms configured to adjust the speed set point at which the one or more displaceable components are displaced;
   providing a data processing device operatively coupled to the one or more speed adjustment mechanisms, the data processing device configured to generate a stochastic signal for introducing a perturbation to the one or more displaceable components, the stochastic signal oscillating above and below a base velocity signal, and the data processing device further configured to control the speed set point of the one or more displaceable components using the stochastic signal such that the one or more displaceable components perturb a gait of the person;
   positioning the person on one or more respective surfaces of the one or more displaceable components of the gait perturbation device;
   generating, by using the data processing device, a stochastic signal for introducing a perturbation to the one or more displaceable components of the gait perturbation device;
   controlling, by using the data processing device, the speed set point of the one or more displaceable components of the gait perturbation device using the stochastic signal that oscillates above and below a base velocity signal; and
   displacing, by using the one or more speed adjustment mechanisms, the one or more displaceable components of the gait perturbation device based upon the speed set point determined using the stochastic signal such that the one or more displaceable components randomly perturb a gait of the person.

19. The method according to claim 18, further comprising the steps of:
   providing at least one input device operatively coupled to the data processing device, the at least one input device configured to enable a user to manually input at least one of: (i) an amplitude of the stochastic signal, (ii) a frequency of the stochastic signal, and (iii) a signal type of the stochastic signal, the signal type of the stochastic signal being selected from the group consisting of a uniform signal and a random signal;
   receiving, at the data processing device, the at least one of: (i) the amplitude of the stochastic signal, (ii) the frequency of the stochastic signal, and (iii) the signal type of the stochastic signal from the at least one input device; and
   generating, by using the data processing device, the stochastic signal based upon at least one of: (i) the amplitude of the stochastic signal, (ii) the frequency of the stochastic signal, and (iii) the signal type of the stochastic signal.

20. The method according to claim 19, wherein the stochastic signal generated by the data processing device comprises a uniform stochastic signal or a normal stochastic signal, wherein the data processing device is configured to generate the stochastic signal based upon the amplitude of the stochastic signal input by the user, and at least one of: (i) the frequency of the stochastic signal input by the user, and (ii) the signal type of the stochastic signal input by the user; and wherein the method further comprises the step of:
   computing the uniform stochastic signal or the normal stochastic signal as a function of a randomly generated uniform signal and the amplitude input by the user.

* * * * *